United States Patent
Dolensky et al.

(10) Patent No.: US 8,147,597 B2
(45) Date of Patent: Apr. 3, 2012

(54) OXYGEN CONCENTRATION SYSTEM

(75) Inventors: Joseph T. Dolensky, Kennesaw, GA (US); Marvin Zeigler, Woodstock, GA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 12/831,521

(22) Filed: Jul. 7, 2010

(65) Prior Publication Data

US 2010/0269701 A1   Oct. 28, 2010

Related U.S. Application Data

(62) Division of application No. 11/636,235, filed on Dec. 8, 2006, now Pat. No. 7,763,103.

(60) Provisional application No. 60/840,523, filed on Aug. 28, 2006.

(51) Int. Cl.
*B01D 53/02* (2006.01)
(52) U.S. Cl. ............................................. 96/130; 96/143
(58) Field of Classification Search .............. 95/96, 148; 96/130, 143; 128/205.12, 205.27
See application file for complete search history.

(56) References Cited

U.S. PATENT DOCUMENTS

| | | | |
|---|---|---|---|
| 4,502,873 A | 3/1985 | Mottram et al. | |
| 4,627,860 A | 12/1986 | Rowland | |
| 5,746,806 A | 5/1998 | Aylsworth et al. | |
| 5,858,062 A | 1/1999 | McCulloh et al. | |
| 5,906,672 A | 5/1999 | Michaels et al. | |
| 5,917,135 A | 6/1999 | Michaels et al. | |
| 5,997,617 A * | 12/1999 | Czabala et al. | 96/130 |
| 6,383,256 B1 | 5/2002 | Phillips | |
| 6,475,265 B1 * | 11/2002 | Baksh et al. | 95/96 |
| 7,087,101 B2 | 8/2006 | Murley et al. | |
| 2002/0029691 A1 | 3/2002 | McCombs et al. | |
| 2002/0033095 A1 | 3/2002 | Warren | |
| 2003/0192431 A1 | 10/2003 | Lee et al. | |
| 2006/0048644 A1 | 3/2006 | Dolensky et al. | |
| 2006/0062707 A1 | 3/2006 | Crome et al. | |

OTHER PUBLICATIONS

PCT Search Report and Written Opinion, Jan. 25, 2008.

* cited by examiner

*Primary Examiner* — Robert A Hopkins
(74) *Attorney, Agent, or Firm* — Michael W. Haas

(57) ABSTRACT

The present system is an adsorption system (100) for separating air into a concentrated gas component, which has an air supply, a compressor (115) for receiving and compressing the air supply, providing a compressed air supply, and molecular sieve material for separating the compressed air supply into a concentrated gas component. The adsorption system delivers at least 5 liters per minute (LPM) of concentrated gas component from the molecular sieve material in which the system has a specific total weight per LPM<9 lbs/LPM. Additionally, an output quantity of the concentrated gas is delivered by the adsorption system and a purging quantity of the concentrated gas is dispensed into a sieve chamber of the adsorption system undergoing a purge cycle. The purging quantity has a value equal to or less than the difference between the maximum quantity and the output quantity, and the purging quantity is controlled based on the output quantity.

11 Claims, 23 Drawing Sheets

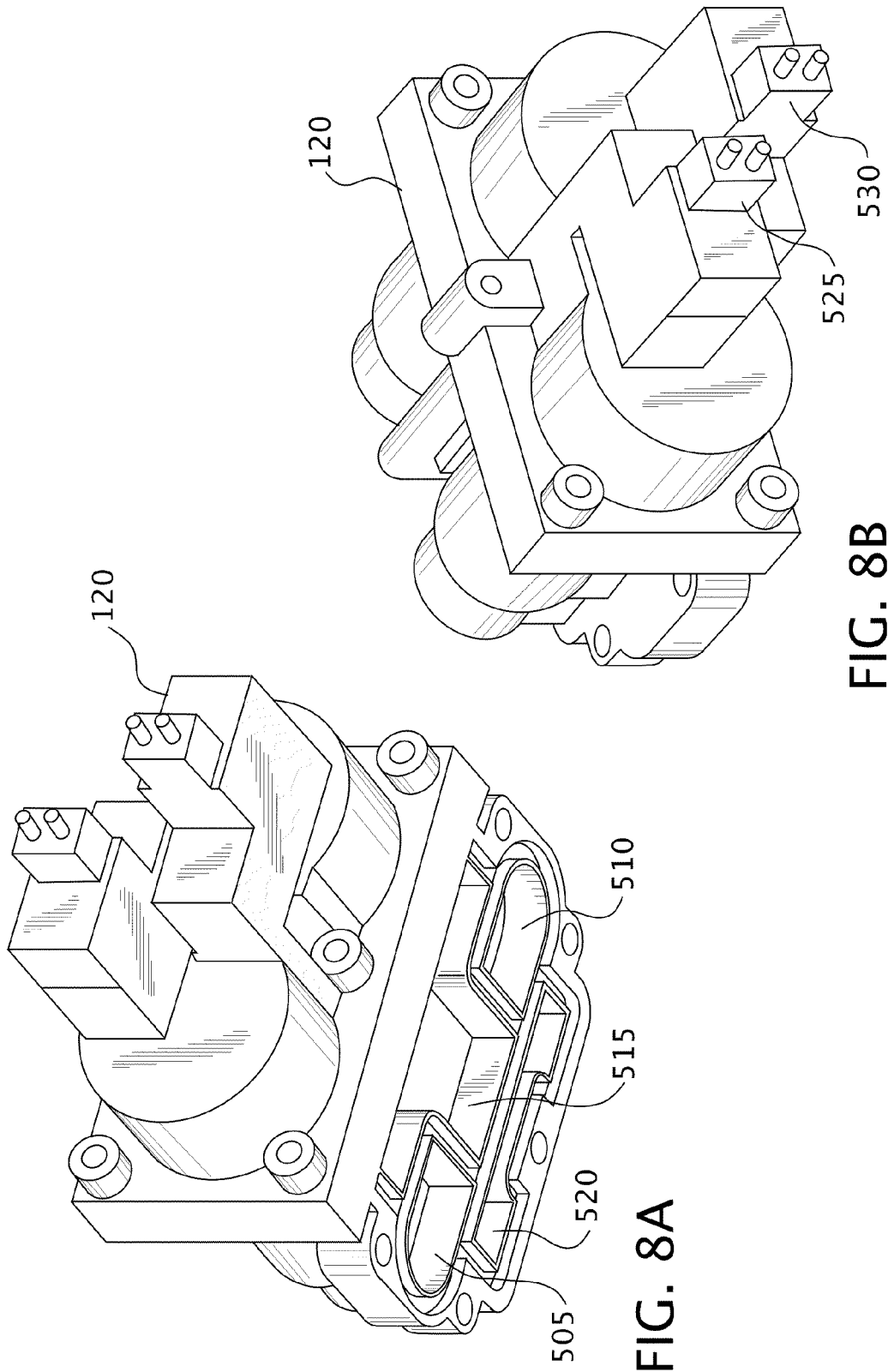

OXYGEN CONCENTRATION SYSTEM

CROSS-REFERENCE TO RELATED APPLICATIONS

This application is a Divisional under 35 U.S.C. §120 of U.S. patent application Ser. No. 11/636,235, filed Dec. 8, 2006, which claims priority under 35 U.S.C. §119(e) from provisional U.S. patent application No. 60/840,523, filed Aug. 28, 2006, the contents of which are incorporated herein by reference.

BACKGROUND OF THE INVENTION

1. Field of the Invention

This invention relates to a pressure swing adsorption system, and, more particularly, to an oxygen concentrator system having a multi-chamber canister for receiving compressed air from a compressor and directing the air through a series of chambers integral within a single assembly for producing concentrated oxygen in a pressure swing adsorption system, which system provides 5 LPM at an oxygen concentration of at least 90%.

2. Description of the Related Art

Adsorption separation processes depend on the ability of certain solids to selectively adsorb one or more components from a gaseous mixture. In oxygen concentrators for patient use, the adsorption separation processes are usually fixed bed operations, including two main steps, the adsorption step and the desorption step.

Pressure Swing Adsorption (PSA) is a useful technique for separating components of gaseous mixtures in such medical uses. A gaseous mixture, typically ambient air, is fed into a chamber, where the components are separated, producing a stream with a high percentage of one component. Air contains many components, namely approximately 21% oxygen, 78% nitrogen, 0.9% argon and 0.1% other trace gases. PSA can be used to separate the oxygen from the inlet air, to supply the patient with higher concentrations of oxygen.

Generally, such component separation in the chamber is achieved by using a zeolite, or molecular sieve, which has a selective affinity for adsorbing a certain component in the mixture. Zeolites are natural or synthetically produced molecular sieves that have uniform pores or crystalline cavities. Chemical components small enough to fit into the zeolite's pores are adsorbed onto the surface of the zeolite material. How readily a component adsorbs onto the zeolite depends on the shape and size of the molecule compared to the shape and size of the pores in the zeolite pellet. A zeolite can adsorb a molecule of any diameter up to its own pore size.

Pressure Swing Adsorption relies on swings in pressure to cycle the chamber sequentially from selective adsorption to desorption. This swing can occur from high pressure to atmospheric pressure or from atmospheric pressure to vacuum. If the swing occurs from atmospheric pressure to vacuum, it is technically considered Vacuum Pressure Swing Adsorption (VPSA). It is well known to those of skill in the art the PSA and VPSA techniques for component separation are quite different, each technique with its own attendant benefits and deficiencies.

A typical pressure swing adsorption system is an oxygen concentrator that separates the oxygen from air for subsequent inhalation by a patient. Conventional systems provide between 0.5 liters per minute (LPM) and 10 LPM. Such oxygen concentrators include a plurality of molecular sieve beds for separating the gas into an oxygen and a nitrogen fraction whereby the oxygen is subsequently provided to a patient while the nitrogen is retained in the sieve bed and subsequently purged. These oxygen concentrators include several components such as an air compressor, two three-way air valves, multiple canisters each housing a separate molecular sieve and a product reservoir tank. Such structures require extensive valving and plumbing which affects the efficiency and costs of these systems.

Some PSA systems of the prior art include a multi-chamber canister for a pressure swing adsorption system which includes at least three chambers. The canister includes a housing of a general length. A first molecular sieve chamber is disposed within the housing for receiving a first molecular sieve for separating air from the ambient environment into a concentrated gas component. At least a second molecular sieve-chamber is also disposed within the housing for receiving a second molecular sieve for separating air from the ambient environment into a concentrated gas component. A supply chamber is disposed within the housing for receiving air from the ambient environment and for communicating the air to either the first or second molecular sieve chamber.

While many conventional systems are capable of delivering sufficient flow rates to meet the patient's need, they do not meet many of the patients' demands including the desire for high efficiency, high product gas concentrations, and low weight. For example, many of the conventional systems require a significant amount of molecular sieve materials and power to operate. Other systems provide oxygen at insufficient purities at certain flow rates. Some conventional systems have implemented features and methods which attempt to address some of these insufficiencies.

For example, U.S. Pat. No. 6,683,256 ("the '256 patent") discloses a molecular sieve type gas separation apparatus that alters the duration of the desorption regeneration phase and the adsorption generation phase according to the desired concentration of product gas. More particularly, the '256 patent discloses an adaptive control method for a gas separation apparatus that uses an oxygen sensor responsive to the concentration constituent of the product gas. Based on the data received from the oxygen sensor, the gas separation apparatus can modify the duration of the adsorption generation phase and the desorption regeneration phase. If the sensor indicates that the concentration constituent of the product gas is higher than desired, then the desorption phase can be shortened and thus the requirements for the supply of input gas can be decreased.

Similarly, U.S. Pat. No. 5,906,672 ("the '672 patent") discloses an oxygen concentrator that incorporates a microprocessor to evaluate the output of product gas from the oxygen concentrator. Additionally, the device provided includes a closed-loop feedback circuit to evaluate the durations of the phase of the pressure swing adsorption cycle. The microprocessor instructs the device to incrementally increase the valve timing until a decrease in oxygen output is sensed. When a decrease in oxygen output is detected, the microprocessor instructs the device to step back to the previous timing.

U.S. Pat. No. 4,627,860 ("the '860 patent") discloses a oxygen concentrator and test apparatus. The '860 patent teaches using a microprocessor to monitor the sensing functions and performance of various components of the concentrator. Furthermore, the '860 patent teaches a test apparatus in communication with the concentrator to display the selected monitored functions of the concentrator. The test apparatus allows the operator to monitor the performance levels of the machine and diagnose component problems.

U.S. Pat. No. 5,474,595 ("the '595 patent") discloses a pressure swing adsorption apparatus with a capacity control system for the compressor. The capacity control system provides a mechanical valve within the housing of the unit which can be manually set to restrict the intake of ambient air into the compressor. The restricted quantity of ambient air reduces the load on the compressor and thus the power consumed by the system.

While the systems of the prior art are suitable for their intended purposes, they are not capable of delivering a reliable oxygen concentration of 90% or more at 5 LPM in a system with minimal weight, size, sound level and power consumption characteristics. Furthermore, the prior art does not describe a device which is capable of generating the maximum oxygen concentration purity possible for flow rates from 0 to 5 LPM. Moreover, the prior art does not teach a system capable of operating at minimum power requirements at flow rates from 0 to 5 LPM. Additionally, the prior art does not teach a system capable of operating in both a low power mode and an increased oxygen mode. It is to such an oxygen concentration system that the present invention is primarily directed.

SUMMARY OF THE INVENTION

Accordingly, it is an object of the present invention to provide an adsorption system that overcomes the shortcomings of conventional adsorption systems. This object is achieved according to one embodiment of the present invention by providing an adsorption system for separating air into a concentrated gas component that includes an air supply, a compressor for receiving and compressing the air supply to provide a compressed air supply, and molecular sieve material for separating the compressed air supply into a concentrated gas component. Furthermore, the adsorption system delivers at least 5 liters per minute (LPM) of concentrated gas component from the molecular sieve material in which the system has a specific total weight per LPM<9 lbs/LPM.

In another embodiment, an adsorption system is provided for separating air into a concentrated gas component that includes a compressor, a molecular sieve material for separating the compressed air supply into a concentrated gas component, and an outlet that delivers at least 5 LPM of concentrated gas component from the molecular sieve material. The molecular sieve material has total weight, and the adsorption system has a specific total molecular sieve material weight per LPM$\leq$0.7 lbs/LPM.

In a still further embodiment, an adsorption system is provided for separating air into a concentrated gas component that includes a compressor, a molecular sieve material, and an outlet that delivers at least 5 LPM of concentrated gas component from the molecular sieve material. The adsorption system of this embodiment has total volume, and a specific volume per LPM<0.40 ft$^3$/LPM.

In yet another embodiment, an adsorption system is provided for separating air into a concentrated gas component that includes a compressor, a molecular sieve material, and an outlet that delivers at least 5 LPM of concentrated gas component from the molecular sieve material. This adsorption system produces a sound level during operation, and has a specific sound level per LPM$\leq$9.5 dBA/LPM.

In another embodiment, an adsorption system is provided for separating air into a concentrated gas component that includes a compressor, a molecular sieve material, and an outlet that delivers at least 5 LPM of concentrated gas component from the molecular sieve material. The adsorption system utilizes power during operation, and has a specific power level per LPM$\leq$80 W/LPM.

In yet another embodiment, an adsorption system is provided for separating air into a concentrated gas component that includes a compressor, a molecular sieve material, and an outlet that delivers at least 95.7% pure concentrated gas component from the molecular sieve material.

In a further embodiment, an adsorption system is provided for separating air into a concentrated gas component that includes a compressor, a molecular sieve material, a first molecular sieve chamber for receiving the molecular sieve material, a second molecular sieve chamber for receiving the molecular sieve material, and a supply chamber for receiving the compressed air supply and for communicating the compressed air supply to the first and the second molecular sieve chambers. The system also includes an outlet delivering a concentrated gas component from the molecular sieve material, and a fixed orifice for communicating the concentrated gas component between the first molecular sieve chamber and the second molecular sieve chamber. The molecular sieve material has a total molecular sieve material weight, and the total molecular sieve material weight per square inch of the area of the fixed orifice <3,000 lbs/square inch.

In a still further embodiment, an adsorption system is provided for separating air into a concentrated gas component that includes a compressor for receiving and compressing air from an air supply, providing a compressed air supply, a molecular sieve material, a first molecular sieve chamber for receiving the molecular sieve material, a second molecular sieve chamber for receiving the molecular sieve material, a supply chamber for receiving the compressed air supply and for communicating the compressed air supply to the first and the second molecular sieve chambers, and an outlet delivering a concentrated gas component from the molecular sieve material. The capacity of the compressor is matched to the capacity of the molecular sieve material.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 8A and 8B are bottom and top perspective views, respectively, of a valve in the pressure swing adsorption system of FIGS. 2A and 2B according to the principles of the present invention;

DETAILED DESCRIPTION OF EXEMPLARY EMBODIMENTS

Figure 1:
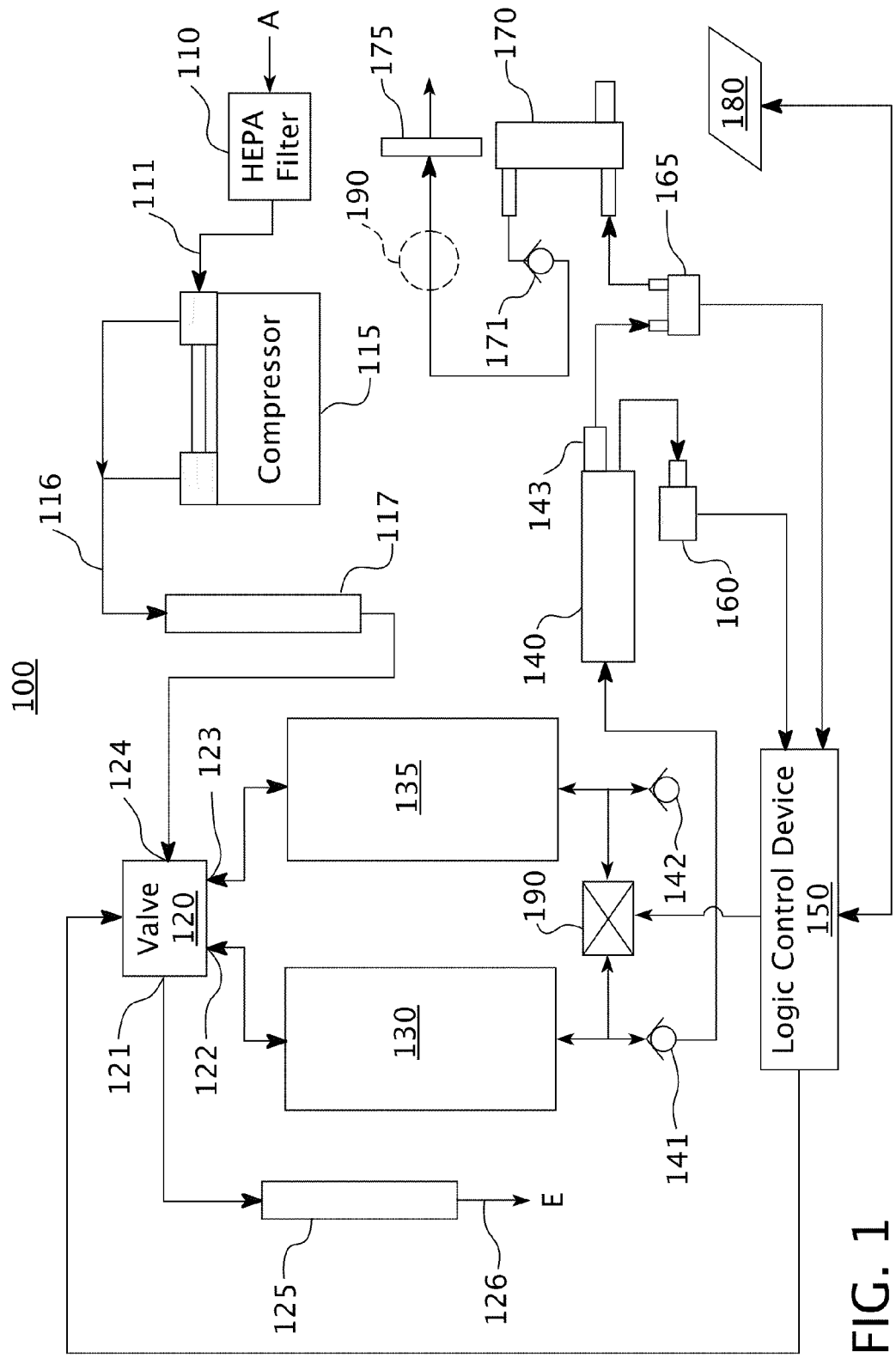
FIG. 1 is a schematic diagram of a pressure swing adsorption system according to the principles of the present invention.

Referring now in detail to the drawing figures, wherein like reference numerals represent like parts throughout the several views. FIG. 1 illustrates a schematic (block) diagram of a pressure swing adsorption system 100 in accordance with an embodiment of the present invention. Pressure swing adsorption system 100 includes some standard components that are known to those in the art. The operation and design of the conventional aspects of pressure swing adsorption system 100 are described in U.S. Pat. Nos. 5,183,483 and 5,997,617, both of which are hereby incorporated by reference. Those of skill in the art will appreciate that while the disclosure herein may focus on the pressure swing adsorption systems for the generation of oxygen, the embodiments of the present invention incorporate and apply to many different types of pressure swing adsorption systems.

The terms "molecular sieve chamber", "sieve chamber", and "sieve bed" are used synonymously herein to refer to devices capable of storing molecular sieve materials for use in the separation of gas components. The terms "adsorption" and "feed" are used synonymously herein to refer to the process of inserting compressed gas into a molecular sieve chamber for separation. The terms "desorption", "purge", and "regeneration" are used synonymously herein to refer to the process of removing non-product gases from a molecular sieve chamber.

Pressure swing adsorption system 100 of the present invention provides a light weight, small size, low sound level, low power consumption oxygen concentrator that is capable of generating an oxygen output in the range of 0.5 to 5 LPM. To provide these advantages, pressure swing adsorption system 100 relies upon a highly efficient architecture and strategically matched components, including a highly adsorbent molecular sieve and optimized compressor. FIG. 1 provides an illustration of this highly efficient architecture in accordance with an exemplary embodiment of the present invention.

The input to pressure swing adsorption system 100 is ambient air "A." This air A is most often untreated atmospheric air. However other sources for an input gas, such as gas stored in a pressurized container are contemplated by the present invention. Pressure swing adsorption system 100 includes a filter 110 to initially filter in the input air A. Filter 110 can be a High Efficiency Particulate Absorbing ("HEPA") filter that is typically composed of a mat of randomly arranged fibers that can collect the contaminants in the ambient air A. Filter 110 is capable of filtering a significant portion of the contaminants in the ambient air A, including dust, pollen, mold, bacteria, and any sufficiently large particles. The filtration of the input ambient air A by filter 110 enable the input of clean ambient air into a compressor 115. The present invention also contemplates that a cabinet filter screen (not shown) is provided on the housing of the pressure swing adsorption system. The uncontaminated nature of the air feed into compressor 115 contributes to the efficiency of the compressor and helps prevent the compressor from being clogged and corroded by contaminants in the air processed.

Compressor 115 is capable of providing the pressurization within the pressure swing adsorption system, and, thus, is a central component of the system. Compressor 115 receives a filtered air input 111, compresses the air, and provides an output of air 116 at the pressure required by the pressure swing adsorption system. In an exemplary embodiment, compressor 115 is a twin-head, oiless device. In an alternative embodiment, the compressor is a single head device. The present invention contemplates that the compressor can have other configurations so long as it achieves the operating and/or functional capabilities suitable for use in the system of the present invention.

An exemplary embodiment of compressor 115 provides a device that is matched to the parameters and requirements of the pressure swing adsorption system. For example, and without limitation, the capacity of compressor 115 is specifically matched with the capacity of the sieve chambers of the pressure swing adsorption system. Providing a compressor that is specifically matched to the parameters of the system, results in numerous benefits and contributes to the ability of the pressure swing adsorption system 100 to overcome the deficiencies of the conventional systems.

The sieve chambers of the pressure swing adsorption system 100 are designed to process a predetermined quantity of ambient air at a predetermined air pressure and maintain a certain level of recovery rate of oxygen from the ambient air. In an exemplary embodiment of the pressure swing adsorption system, the sieve chambers are designed to process 70 liters of pressurized ambient air at 20 pounds per square inch (psi) while maintaining a recovery rate of at least 30%. In this exemplary embodiment, pressure swing adsorption system 100 is specifically designed so that compressor 115 matches the capacity specifications of the sieve beds in order to ensure the efficiency of the compressor and the overall pressure swing adsorption system. Specifically, compressor 115 is designed to produce an output that matched the parameters of the sieve chambers.

In an exemplary embodiment, compressor 115 is designed to produce 70 liters of gas a minute at 20 psi to match the capacity of the sieve chambers. The matching of compressor 115 to the capacity of the sieve chambers allows for not only the optimal efficiency of the compressor, but also enables the compressor to be relatively lightweight and require the minimal amount of power necessary to meet the demands of the system. In an exemplary embodiment of the present invention, compressor 115 weighs less than 15 lbs. In some embodiments, the compressor weighs less than 10 lbs.

In exemplary embodiment, the specification for compressor 115 of the pressure swing adsorption system 100 is as provided in Table 1 below:

TABLE 1

| Parameter | Domestic Specification | International Specification |
|---|---|---|
| Motor Voltage & Frequency | 120 V +/− 10% 60 Hz | 230 V +/− 10% 50 Hz |
| Minimum Flow at 15 psig | 70 LPM | 59 LPM |
| Minimum Flow at 20 psig | 66 LPM | 56 LPM |
| Minimum Flow at 25 psig | 62 LPM | 52 LPM |
| Stall Voltage at 20 psig | 108 V | 207 V |
| Sound Level at 1 m | 58 dBA | 58 dBA |

In accordance with the Ideal Gas Law, PV=nRT (pressure*volume=number of moles of gas*gas constant*temperature), an increase in pressure of air results in an increase in the temperature of the air compressed. Therefore, an output 116 of compressor 115 is typically at an elevated temperature. To alleviate this heat, output 116 can be connected to a heat exchanger 117 in some embodiments. Heat exchanger 117 can be configured to provide for the efficient heat transfer of the air in output 116 of compressor 115. In other words, the temperature of the air in output 116 of the compressor can be reduced by heat exchanger 117.

After leaving heat exchanger 117, the compressed input air can pass to a main process valve 120. Main process valve 120 is used to communicate the flow of gases throughout the pressure swing adsorption cycle. Those of skill in the art will appreciate that process valve 120 can be implemented with a variety of different devices. For example, U.S. Pat. No. 6,062,260 ("the '260 patent") discloses an SMC® sure cycle valve suitable for implementation as main process valve 120. In some embodiments, main process valve 120 can be controlled by a logic control device 150. Logic control device 150 can include a microprocessor that is capable of monitoring and giving instructions to main process valve 120. In a non-limiting example, main process valve 120 is operated by solenoids and logic control unit 150 is capable of controlling those solenoids. In some embodiments the solenoids have minimum switching pressure between 5 to 8 psi. As with compressor 115, logic control device 150 can instruct the operation of main process valve 120 according to a set of predetermined parameters for a pressure swing adsorption cycle at a given LPM output.

In an exemplary embodiment, main process valve 120 includes four ports, a first port, exhaust port 121, that is connected to an exhaust device 125; a second port 122 that is connected to a first sieve chamber 130; a third port 123 that is connected to a second sieve chamber 135; and a fourth port, supply input port 124, that is connected to heat exchanger 117. Ports, 121, 122, 123, and 124, permit main process valve 120 to connect a number of different flow pathways in accordance with operation of the pressure swing adsorption cycle. Ports 122 and 123 connected to the sieve chambers open and close to permit compressed air to enter the respective molecular sieve chambers during operation of the pressure swing adsorption cycle.

In a non-limiting example configuration, main process valve 120 can be configured with supply input port 124 from heat exchanger 117 open, and second port 122 to first sieve chamber 130 open, such that the compressed air is supplied to first sieve chamber 130. Similarly, main process valve 120 can be configured with supply input port 124 open and third port 123 to second sieve chamber 135 open, such that the compressed air is supplied to second sieve chamber 135. Alternatively, main process valve 120 can be configured with both second port 122 and third port 123 open, such that compressed air is supplied to both first sieve chamber 130 and second sieve chamber 135. These configurations of main process valve 120 are used in the adsorption phases of the cycles of pressure swing adsorption system 100. In the adsorption phases, ambient air can be pumped from compressor 115, through main process valve 120, and into either or both of first sieve chamber 130 and second sieve chamber 135.

First sieve chamber 130 and second sieve chamber 135 contains a zeolite material or other suitable material for fractionating air into oxygen and a waste product including nitrogen. Zeolites are highly crystalline alumino-silicate frameworks comprising $[SiO_4]^{4-}$ and $[AlO_4]^{5-}$ tetrahedral units. T atoms (Si, Al) are joined by an oxygen bridges. Introduction of an overall negative surface charge requires counter ions e.g. $Na^+$, $K^+$, and $Ca^{2+}$. The zeolite crystals contain water, and as the water is driven off by heating, there is no discernible collapse of the framework structure. This leads to a highly crystalline, microporous adsorbent that has an internal structure which can be easily tailored to adsorb any number of components. Zeolites have beneficial molecular sieving properties. The pore size distribution can be modified, enabling the zeolite to be used as a so-called molecular sieve. Molecules which are too large to diffuse into the pores are excluded, whereas molecules which have a kinetic diameter smaller than the pore size, diffuse into the pores, adsorb and under certain conditions are capable of undergoing catalytic reactions. An example of this is in the sieving of straight and branched chained hydrocarbons to increase the octane number of gasoline.

In order to enable the present system to deliver a relatively light weight, small size, low sound level, low power consumption PSA oxygen concentrator with an output in the range of 5 LPM, a highly adsorbent molecular sieve preferably is employed. SILIPORITE® molecular sieves are mineral synthetic products (zeolites) with remarkable selective adsorption properties, and are an example of a material suitable for fractionating air into oxygen and a waste product gas such as nitrogen for use with the present system. ATOFINA Chemicals, Inc. distributes and provides technical services for SILIPORITE® Molecular Sieves for its sister company, CECA S.A. of Paris, France Both Nitroxy 51 and Nitroxy 51R in the SILIPORITE® line of molecular sieve materials and the MDX molecular sieve from UOP LLC of Des Plaines, Ill., are suitable for use in the present invention.

The Nitroxy 51, Nitroxy 51R and MDX are molecular sieves that have an increased nitrogen adsorption capacity and an increased selectivity of nitrogen over oxygen, compared to conventional molecular sieves. For example, a conventional molecular sieve, such as Nitroxy 5 has a nitrogen adsorption capacity of 8 Nl/kg and selectivity factor $N_2/O_2$ of 3. In contrast, for example, Nitroxy 51 has a minimum nitrogen adsorption capacity of 18 Nl/kg and a selectivity factor $N_2/O_2$ of at least 6. In short, sieve materials that have a nitrogen adsorption capacity of at least 18 Nl/kg and a selectivity $N_2/O_2$ of at least 6 (i.e., a selectivity of 6 or more), are suitable for use in the present invention.

In the adsorption, or feed, phases of the cycle the ambient air A can be separated into product gases, essentially oxygen and argon, and waste product gases including nitrogen, water vapor, and other trace gases. The zeolite material of the sieved chambers, such as chambers 130 and 135, can collect the waste product gases within its pores on the surface of the material when the appropriate pressure is created within the sieve chamber. The oxygen can remain in the sieve chamber as an unattached gas.

In addition to the adsorption phase configurations, main process valve 120 can be configured for various purge, or desorption, phases. In one purge configuration, first port 121 to exhaust device 125 is open, and second port 122 to first sieve chamber 130 is open. This configuration of main process valve 120 allows for the purging of first sieve chamber 130. In an exemplary embodiment, pressure swing adsorption system 100 includes an exhaust device 125 that is capable of pulling the gas contained in sieve chambers 130 and 135 and emitting the gas via an exhaust port 126. Exhaust device 125 can be an exhaust muffler or blown down device or other devices capable of drawing gas from the sieve chambers.

The desorption phase of an oxygen concentrator involves the removal of the waste product gases from sieve chambers 130 and 135. In this manner, the sieve chambers can be relieved of the waste product gas molecules contained within the pores of the sieves and be renewed so as to accept new waste product gas molecules from the next injection of ambient air. Therefore, the capacity of sieve chambers 130 and 135 is directly dependent on the desorption phase.

First sieve chamber 130 and second sieve chamber 135 are also connected to two check valves: a first check valve 141; and a second check valve 142. Check valves 141 and 142 are connected to a product tank 140, which stores the product gas. Check valves 141 and 142 regulate the flow of product gas from sieve chambers 130 and 135 into product tank 140. In one embodiment, check valves 141 and 142 are configured to allow the product gas to flow into product tank 140 when the pressure of the product gas coming from sieve chambers 130 and 135 is greater than the pressure of the product tank. Additionally, check valves 141 and 142 can be configured to prevent backflow of product gases.

A purge control device 190 connects the two outputs of first sieve chamber 130 and second sieve chamber 135. Purge control device 190 can be a passive orifice of a fixed diameter restriction in some embodiments. Additionally, purge control device 190 can be an active valve capable of being controlled by logic control device 150. In an exemplary embodiment, purge control device 190 is operated by solenoids and logic control unit 150 is capable of controlling those solenoids. Therefore, an active purge control device 190 allows for controlled passage of gas between first sieve chamber 130 and second sieve chamber 135.

In the exemplary embodiment depicted in FIG. 1, purge control device 190 is on the product gas side of first sieve chamber 130 and second sieve chamber 135, such that the gas flowing through the purge control device from one sieve chamber to another is product gas. Purge control device 190 can be used in various stages of the pressure swing adsorption cycle. In an exemplary embodiment, purge control device 190 is used to transfer product gas from a sieve chamber in adsorption into a sieve chamber in desorption to aid in the desorption process.

As shown in FIG. 1, product tank 140 can include a pressure regulator 143. Pressure regulator 143 is used to control the flow of product gas to the output. In some embodiments, such as the one depicted in FIG. 1, product tank 140 can be connected to a pressure sensor 160. Pressure sensor 160 is capable of providing information, which can be used in estimating the flow rate of pressure swing adsorption system 100.

In an exemplary embodiment, pressure sensor 160 is enabled to communicate and send information to logic control device 150. In an exemplary embodiment, logic control device 150 performs a calculation based on the data received from the pressure sensor 160 to estimate the flow rate of pressure swing adsorption system 100.

Figure 2:
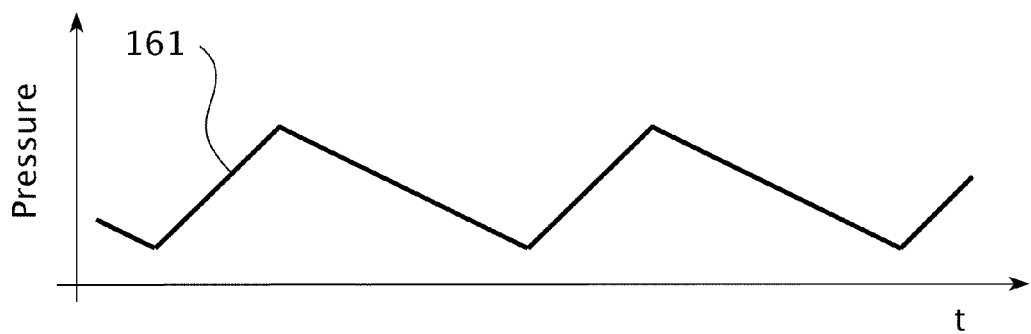
FIG. 2 is a chart showing the typical pressure in a PSA product tank during the PSA process.

There is often a need to optimize the PSA process based on the flow rate of oxygen output from the system. Optimization is achieved by continuously adjusting the valve timing as a function of flow. Because a true flow transducer is costly to add to a commercially viable system, the present invention contemplates estimating the flow rate of oxygen output from the system indirectly via transformations of the pressure in product tank 140, i.e., a pressure signal output by pressure sensor 160. FIG. 2 shows the pressure signal 161 provided by pressure sensor 160 during typical PSA cycles.

Specifically, the flow is directly proportional to the magnitude of the negative slope of the pressure signal. Thus, the actual flow rate of the output from system (FlowLPM) at any time can be computed from the pressure signal as follows:

$$\text{FlowLPM} = K \times ABS(\text{Slope}), \quad (1)$$

where K is a constant, and ABS(Slope) is the absolute value of the slope of the pressure signal.

Figure 3:
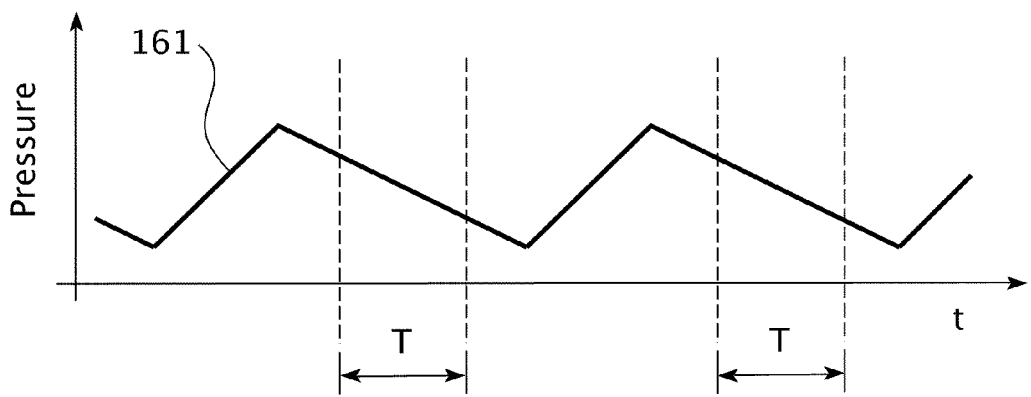
FIG. 3 is the same chart showing examples of window "T" when the slop of the pressure signal is taken for flow estimating purposes.

Calculating the flow is accomplished by converting the signal from pressure sensor 160, conditioning the converted signal, sampling the conditioned signal, and then computing the slope magnitude, over a fixed time window T, on each ½ cycle of the sampled signal. FIG. 3 illustrates this "windowing" process.

Figure 4:
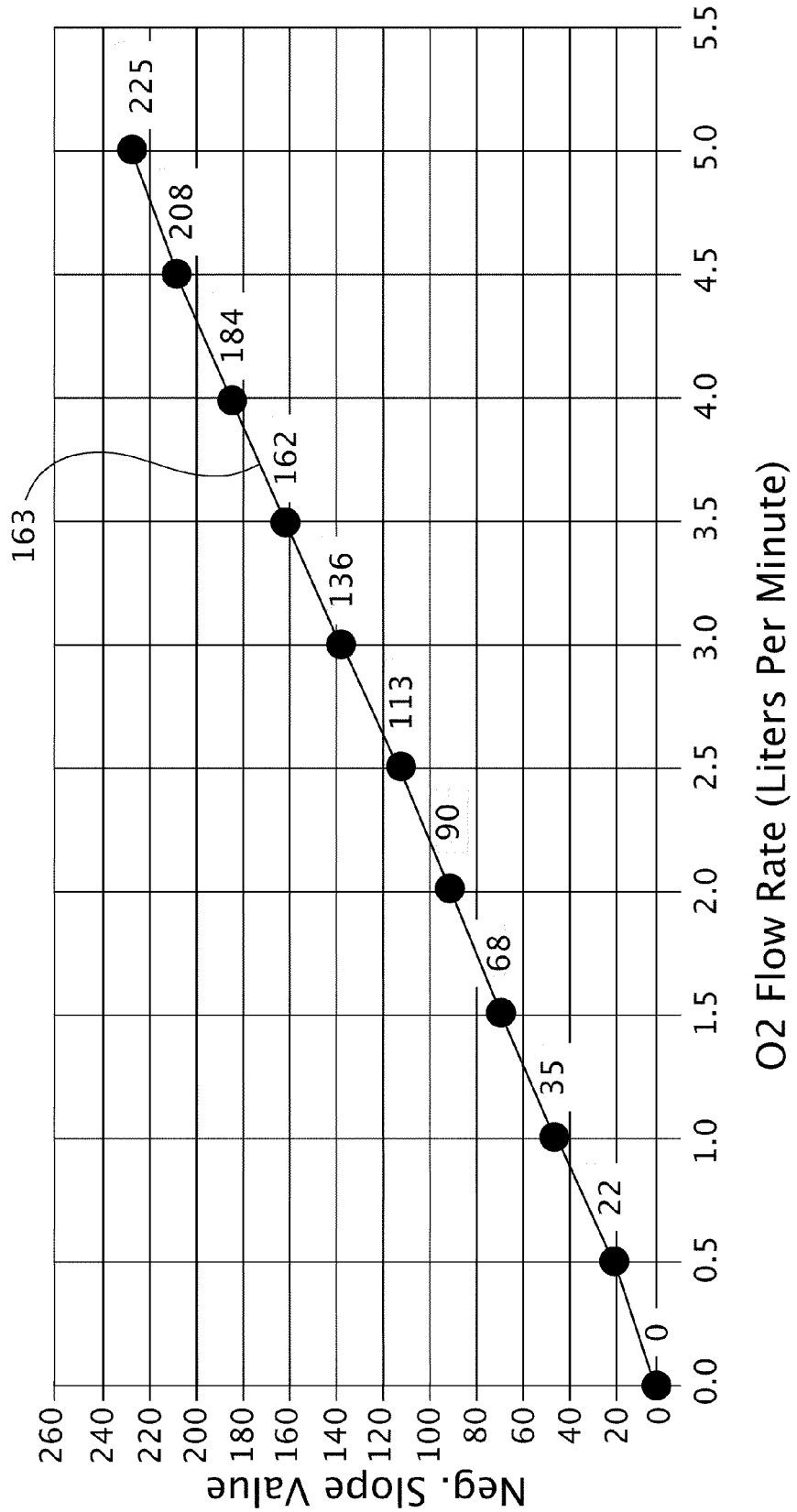
FIG. 4 is a chart illustrating a relationship between the slope of the product tank pressure signal and the oxygen flow rate from the system.

Each computed slope value is averaged with the preceding values using a recursive averaging filter. Because pressure sensor 160 is typically un-calibrated, the output of the averaging filter is scaled and normalized, via two (2) calibration values stored in a non-volatile memory, so as to produce values that are consistent from machine-to-machine. Finally, the computation that results from the scaling/normalization process is the value that corresponds to the actual $O_2$ flow. The result is a linear relationship 163 between negative slope and oxygen output flow rate, as shown, for example, in FIG. 4. Using relationship 163 and/or equation (1), the flow of oxygen from the system can be determined based on the pressure in the product tank, and, in particular, the negative slope of the pressure signal during time period T.

Logic control device 150 can control other devices in the pressure swing adsorption system in accordance with this estimated flow rate. In an exemplary embodiment, the logic control device can alter the operation of purge control device 190 in accordance with the estimate flow rate. In an additional embodiment, the logic control device can modify the pressure swing adsorption cycle based upon the estimated flow rate.

In an exemplary embodiment, pressure regulator 143 is connected to an oxygen sensor 165. Oxygen sensor 165 is further connected to a flowmeter 170. Flowmeter 170 can be used to provide a visual output to the user or monitor of pressure swing adsorption system 100 of the output rate of the system. Flowmeter 170 is connected, through a check valve 171, to an output filter 175. Output filter 175 aids in ensuring the integrity of the product gas being provided to the patient by pressure swing adsorption system 100. Output filter 175 can be a HEPA bacterial filter or other suitable filter. The output port of output filter 175 can be fitted to a device capable of delivering the product gas, or oxygen, to the patient. In some embodiments output filter 175 is connected to a DISS or hose barb fitting from which oxygen is received by the patient.

Figure 5A:
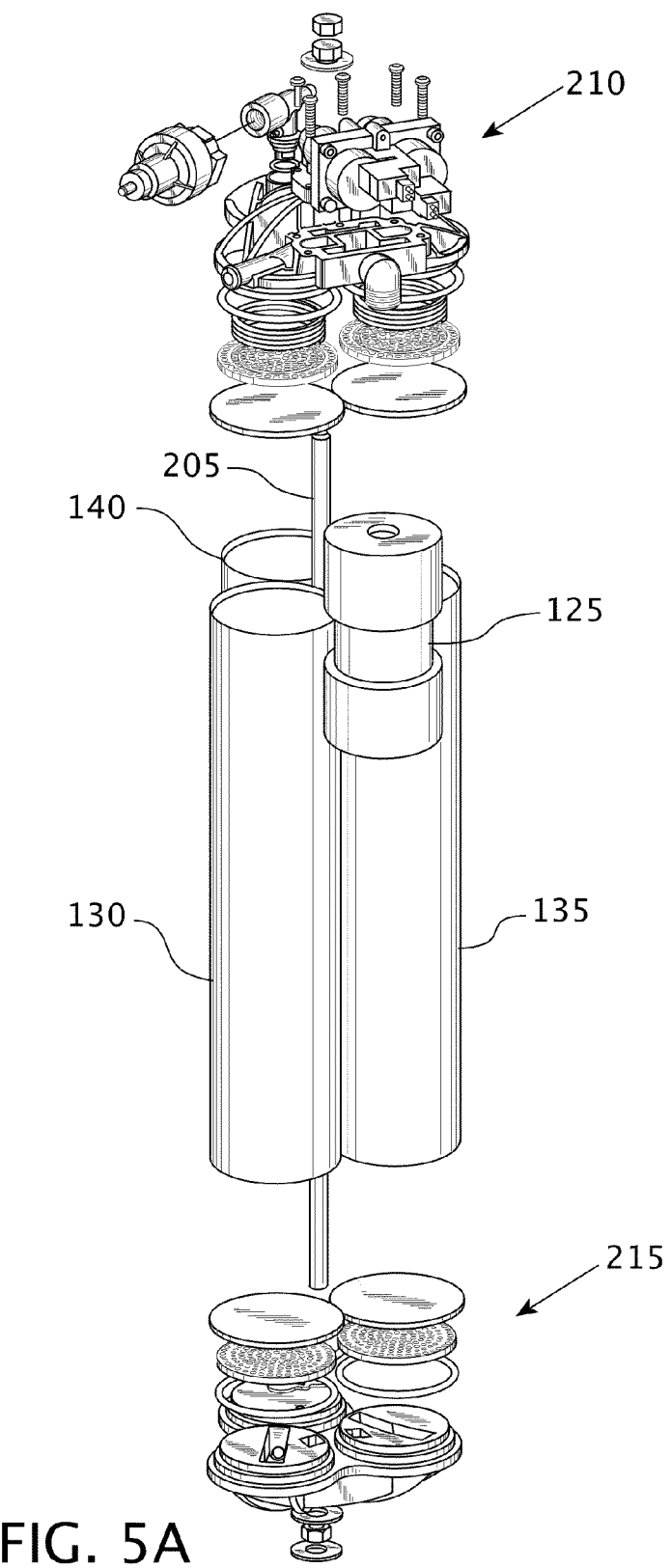
FIGS. 5A and 5B are top and bottom perspective views, respectively, of a portion of the pressure swing adsorption system according to the principles of the present invention.

FIG. 5A is perspective view of a portion of pressure swing adsorption system 100 in accordance with an embodiment of the present invention. FIG. 5A illustrates the assembly of various components of the pressure swing adsorption system. In the exemplary embodiment shown in FIG. 5A, the central portion of the pressure swing adsorption system includes first sieve chamber 130 and second sieve chamber 135. Additionally, the central portion of pressure swing adsorption system 100 can include product tank 140. Product tank 140 is capable of holding the product gas, mainly oxygen, produced by the pressure swing adsorption system. In an exemplary embodiment, product tank 140 does not contain the molecular sieve material. First sieve chamber 130, second sieve chamber 135, and product tank 140 can be fixed upon a mounting rod 205.

A top cover assembly 210 and an end cover assembly 215 are provided in communication with the ends of first sieve chamber 130, second sieve chamber 135, and product tank 140. Top cover assembly 210 and the end cover assembly 215 can be provided with various components to facilitate the functions and operations of the pressure swing adsorption system 100. The top cover assembly 210 and end cover assembly 215 can be attached to mounting rod 205. In an exemplary embodiment, mounting rod 205 is a lightweight yet rigid member capable of bearing the load of the components of pressure swing adsorption system 100.

By enabling a majority of the components of the pressure swing adsorption system to be attached via one mounting rod 205, the weight of system can be reduced by eliminating the need for additional mounting brackets, bolts, and rods, thereby increasing the efficiency of the system. For example, only mounting rod 205 is required, as opposed to a separate bolt, nut, and washer for a majority of the components, to secure a majority of the components of the pressure swing adsorption system.

As shown in FIG. 5A, pressure swing adsorption system 100 also provides an exhaust device 125. Exhaust device 125 is component of the exhaust system that is capable of venting the purged non-product exhaust gas from the pressure swing adsorption system, such as a "blow down" muffler.

Figure 5B:
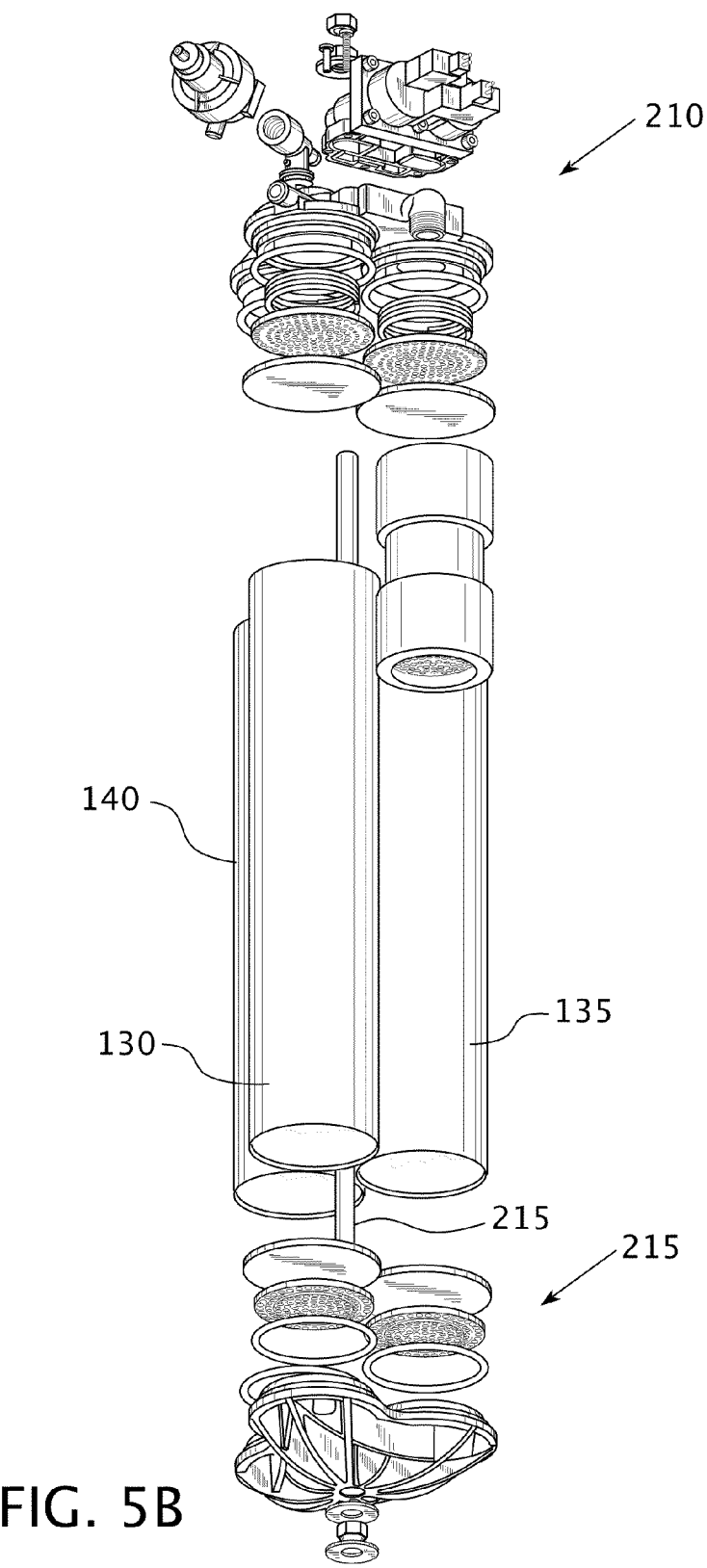

FIG. 5B is perspective of a portion of pressure swing adsorption system 100 in accordance with an embodiment of the present invention. As shown in FIG. 5B, first sieve chamber 130 and second sieve chamber 135 are cylindrical structures. The sieve chambers 130 and 135 are capable of storing the molecular sieve material, such as a natural or synthetic zeolite. In one embodiment, both the first sieve chamber 130 and the second sieve chamber 135 are configured with a synthetic zeolite, such as SILIPORITE® Nitroxy 51R beads. Additionally, product tank 140 is a cylindrical container. In an exemplary embodiment, product tank 140 is simply a hollow cylinder for storing the product gas generated by pressure swing adsorption system 100.

Figure 6A:
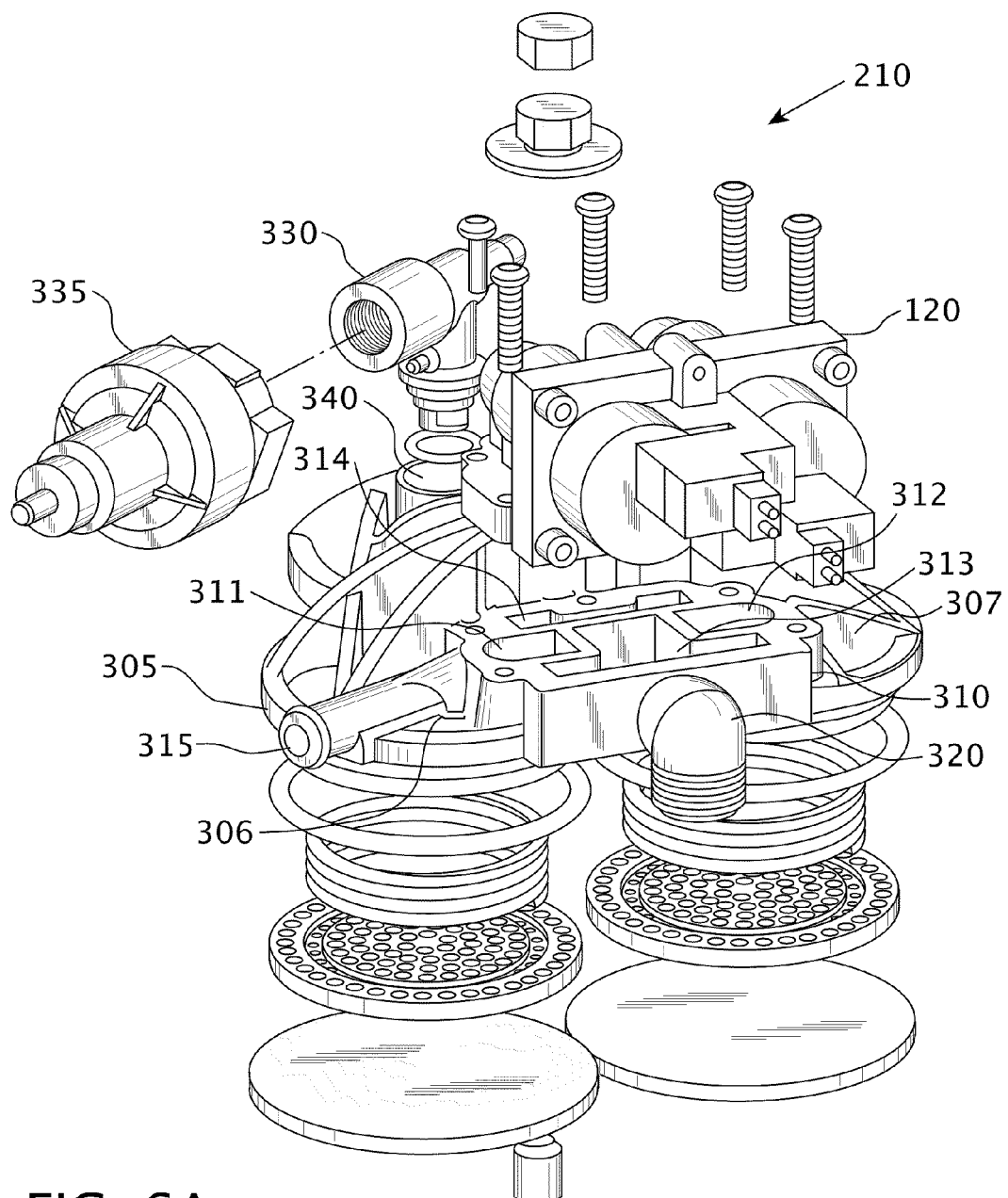
FIGS. 6A and 6B are top and bottom perspective view, respectively, of a top cover assembly in the pressure swing adsorption system of FIGS. 5A and 5B according to the principles of the present invention.

FIG. 6A is a view from a top perspective of top cover assembly 210 in pressure swing adsorption system 100 in accordance with an embodiment of the present invention. Top cover assembly 210 includes a top cover 305. In an exemplary embodiment, top cover 305 is a structure defined by a truss configuration as shown in FIG. 6A. The intricate truss structure of top cover 305 increases the ability of the structure to bear load forces and evenly distribute forces applied to top cover 305. Therefore, the truss configuration of top cover 305 allows the top cover to be constructed of a lightweight material, such as plastic or other polymer. In this manner, top cover 305 further contributes to the lightweight nature of the pressure swing adsorption system.

As shown in FIG. 6A, top cover 305 includes valve mounting surface 310. Top cover 305 also includes a first sieve chamber plenum 306 and a second sieve chamber plenum 307. Disposed within first sieve chamber plenum 306 at a point that aligns with valve mounting surface 310 is a first sieve chamber port 410 (FIG. 7B), which will provide gas flow with first sieve chamber 130. Disposed within the second sieve chamber plenum 307 at a point that aligns with valve mounting surface 310 is a second chamber port 415 (FIG. 7B), which will provide gas flow with second sieve chamber 135. Top cover 305 also includes an exhaust outlet 320. This exhaust outlet communicates with exhaust device 125. Furthermore, disposed within top cover 305 is a supply inlet port 315, which communicates pressurized gas from compressor 115.

In the exemplary embodiment, valve mounting surface 310 can be located within the body of top cover 305. Valve mounting surface 310 includes various ports, which correspond to the aforementioned ports of top cover 305. Valve mounting surface 310 has a valve mounting surface first sieve chamber port 311 that communicates to first sieve chamber 130 and a valve mounting surface second sieve chamber port 312 that communicates to second sieve chamber 135. Valve mounting surface 310 also has a valve mounting surface exhaust port 313 that communicates to exhaust outlet 320 and a valve mounting surface inlet port 314 that communicates with the inlet port 315.

As shown in FIG. 6A, top cover assembly 210 provides a product tank port 340 to the product tank 140. Product tank port 340 enables a fitting 330 to connect the product tank to a pressure regulator 335. In an exemplary embodiment, pressure regulator 335 enables the pressure swing adsorption system to control the output from product tank 140 to provide product gas at a predetermined pressure and flow rate.

Pressure swing adsorption system 100 also includes a valve 120 that is carried by valve mounting surface 310 for communicating the flow of gas throughout the pressure swing adsorption cycle. Valve 120 can be a passive device or it can be an active device. In an exemplary embodiment, valve 120 is capable of being controlled by logic control device 150. The logic control device can send signals and/or instructions to valve 120 to control the opening and closing of the ports of the valve and other operations.

Figure 6B:
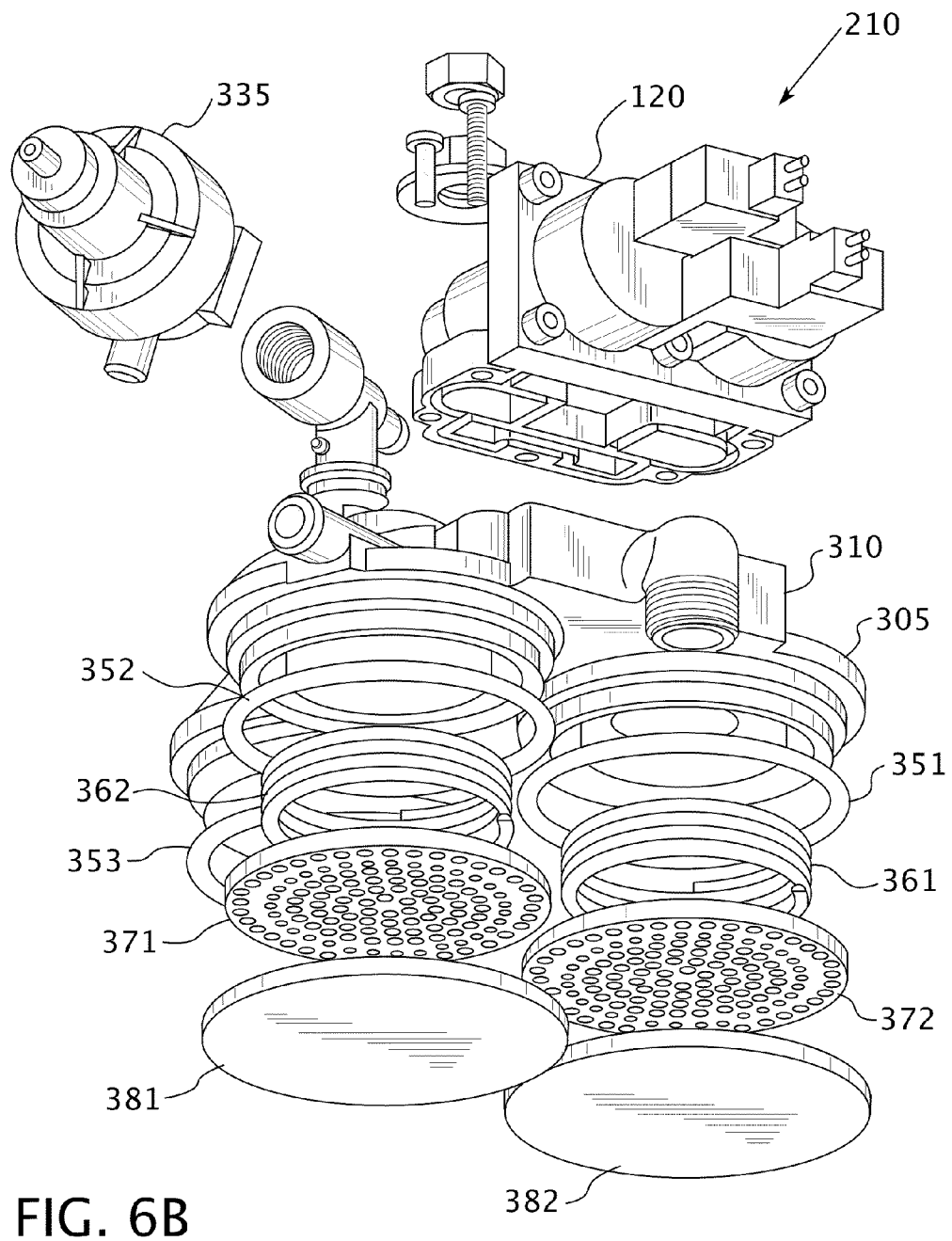

FIG. 6B is a view from a bottom perspective of top cover assembly 210 of pressure swing adsorption system 100 in accordance with an exemplary embodiment of the present invention. The components that connect top cover assembly 210 to first sieve chamber 130, second sieve chamber 135, and product tank 140 are illustrated in this figure. Top cover assembly 210 includes sealant rings, 351, 352, and 353, which enable the top cover to create a sealed connection with first sieve chamber 130, second sieve chamber 135, and product tank 140. Furthermore, springs 361 and 362 are carried by the top cover assembly for maintaining the molecular sieve zeolite material in place within the respective molecular sieve chambers. Top cover assembly 210 includes spring support wafers 371 and 372 to bear the load applied to sieve chambers 130 and 135 by spring 361 and 362. In an exemplary embodiment, top cover assembly 210 also provides passive filtration devices, such as 381 and 382, to filter any large contaminants contained in the gas communicated through the pressure swing adsorption system 100.

Figure 7A:
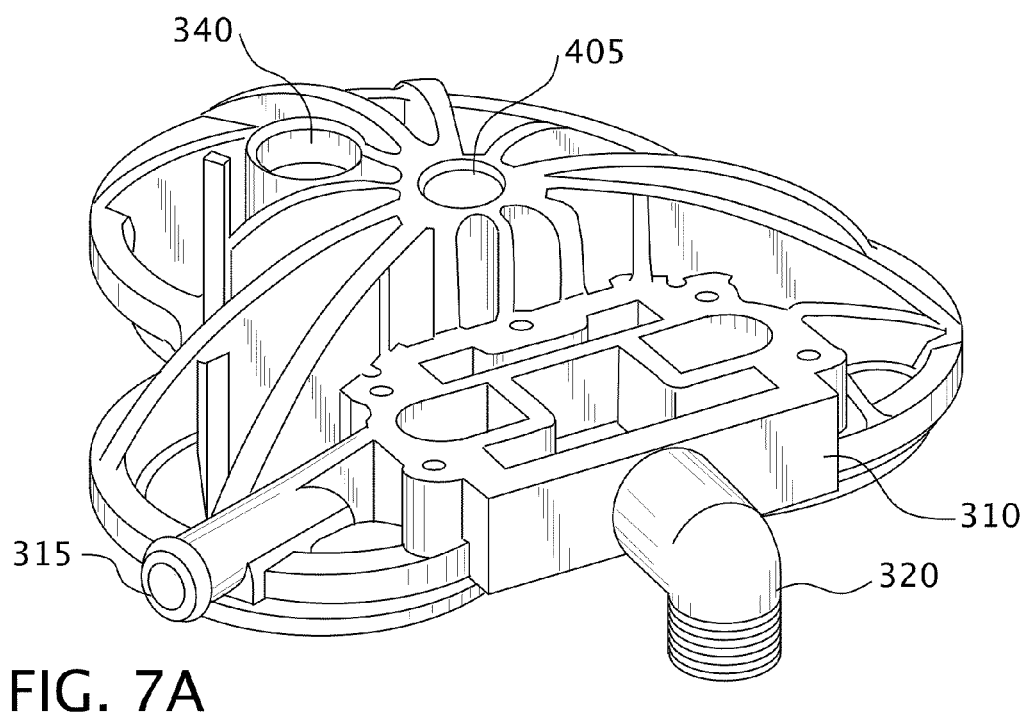
FIGS. 7A and 7B are top and bottom perspective views, respectively, of a top cover in the pressure swing adsorption system of FIGS. 2A and 2B according to the principles of the present invention.

FIG. 7A is a view from a top perspective of top cover 305 that is used in the top cover assembly of FIGS. 6A and 6B in pressure swing adsorption system 100 in accordance with an exemplary embodiment of the present invention. As described, top cover 305 can be configured to include a valve mounting surface 310, a supply inlet port 315, an exhaust outlet 320, and a product tank port 340. As shown in FIG. 7A, these components can be embedded within top cover 305. Furthermore, top cover 305 can provide a mounting conduit 405 through which mounting rod 205 can pass to enable the top cover to be attached to the other components of the pressure swing adsorption system.

Figure 7B:
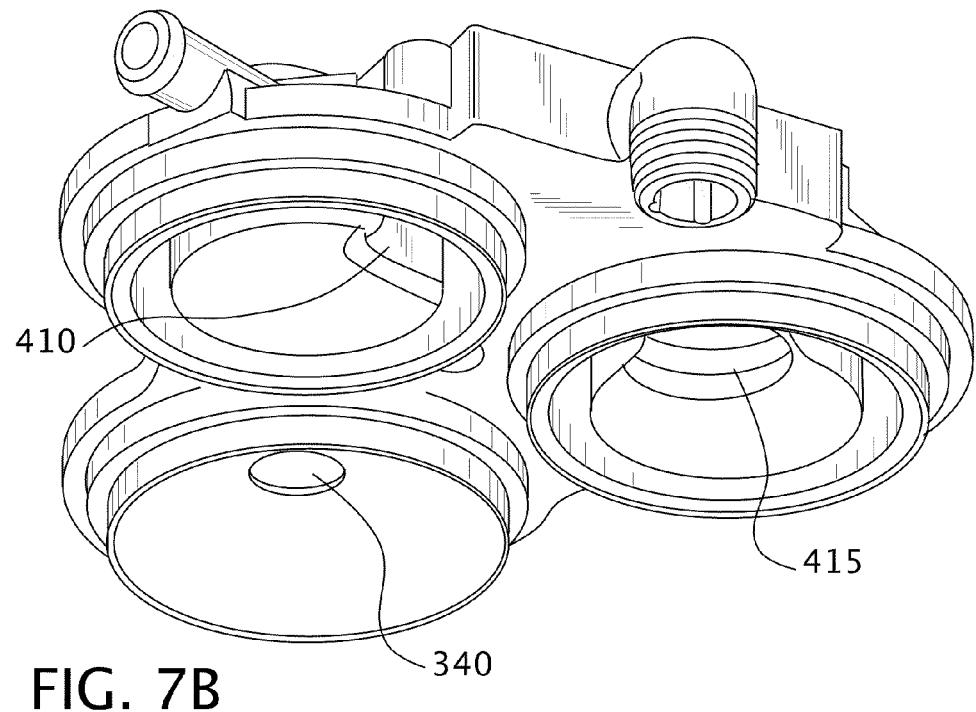

FIG. 7B is a view from a bottom perspective of top cover 305 of the pressure swing adsorption system 100, in accordance with an embodiment of the present invention. FIG. 7B illustrates the conduits in top cover 305 through which gas is permitted to flow. First sieve chamber port 410 in top cover 305 communicates to valve mounting surface first sieve chamber port 311 to permit the flow of gas into the first sieve chamber 130. Second sieve chamber port 415 in top cover 305 communicates to valve mounting surface second sieve chamber port 312 to permit the flow of gas into second sieve chamber 135. Furthermore, product tank port 340 enables product gas to flow from product tank 140, through top cover 305, and to pressure regulator 335.

FIG. 8A is a view from a bottom perspective of valve 120 of the pressure swing adsorption system 100 in accordance with an embodiment of the present invention. The various ports of valve 120 are illustrated in the bottom perspective view shown in FIG. 8A. Valve 120 has ports which match to those of valve mounting surface 310. Valve 120 has a valve first sieve chamber port 505 that communicates to first sieve chamber 130, and a valve second sieve chamber port 510 that communicates to second sieve chamber 135. Valve 120 also has a valve exhaust port 515 that communicates to exhaust outlet 320 and a valve inlet port 520 that communicates with supply inlet port 315. These ports are configured to align with the ports on valve mounting surface 310.

FIG. 8B is a view from a top perspective of valve 120 of pressure swing adsorption system 100 in accordance with an embodiment of the present invention. The valve provides control connections 525 and 530. Signals can be received by the control connections 525 and 530 to direct the operation of the valve 120. In one embodiment, logic control unit 150 provides a control signal to a valve 120. For example, a signal could be received at control connections 525 and 530 to open valve inlet port 520 and valve first sieve chamber 505 and hold all other ports closed, and, thus, allow compressed air to be passed into first sieve chamber 130. Of course, many other combinations of valve operation needed to control the cycling of the sieve beds are contemplated by the present invention.

Figure 9:
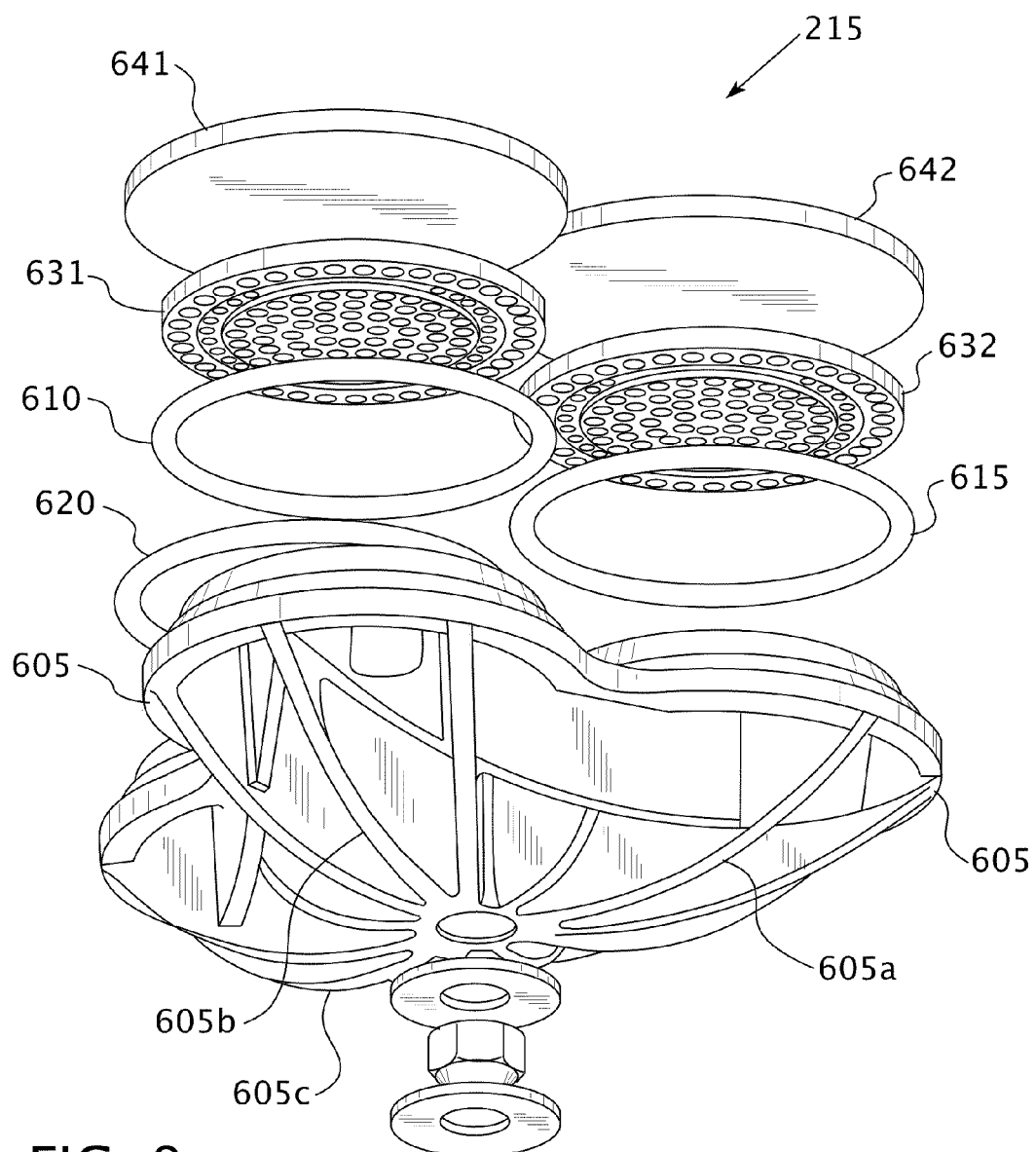
FIG. 9 is a bottom perspective view of an end cover assembly in the pressure swing adsorption system of FIGS. 5A and 5B according to the principles of the present invention.

FIG. 9 is a bottom perspective view of end cover assembly 215 of the pressure swing adsorption system 100 in accordance with an embodiment of the present invention. End cover assembly 215 includes an end cover 605, which, in an exemplary embodiment, is a structure defined by an intricate truss configuration, an example of which is shown in FIG. 9. Each supporting truss member, such as 605*a*, 605*b*, and 605*c*, aid in supporting the rigidity, durability, and strength of end cover 605. As shown in FIG. 9, the truss member, such as 605*a*, creates a triangular-like support element with the bottom portion of end cover 605 serving as the base of the triangle and the center point of the end cover serving as the vertical member of the triangle. The triangular configuration of the truss members of end cover 605 increases the ability of the structure to bear load forces and evenly distribute forces applied to the end cover.

As with top cover assembly 210, end cover assembly 215 includes sealant rings, 610, 615, and 620, to create a sealed connection with first sieve chamber 130, second sieve chamber 135, and product tank 140. End cover assembly 215 includes support wafers 631 and 632 to bear the load applied by sieve chambers 130 and 135. Furthermore, end cover assembly 215 provides passive filtration devices, such as 641 and 642, to filter any large contaminants contained in the gas communicated through pressure swing adsorption system 100.

Figure 10:
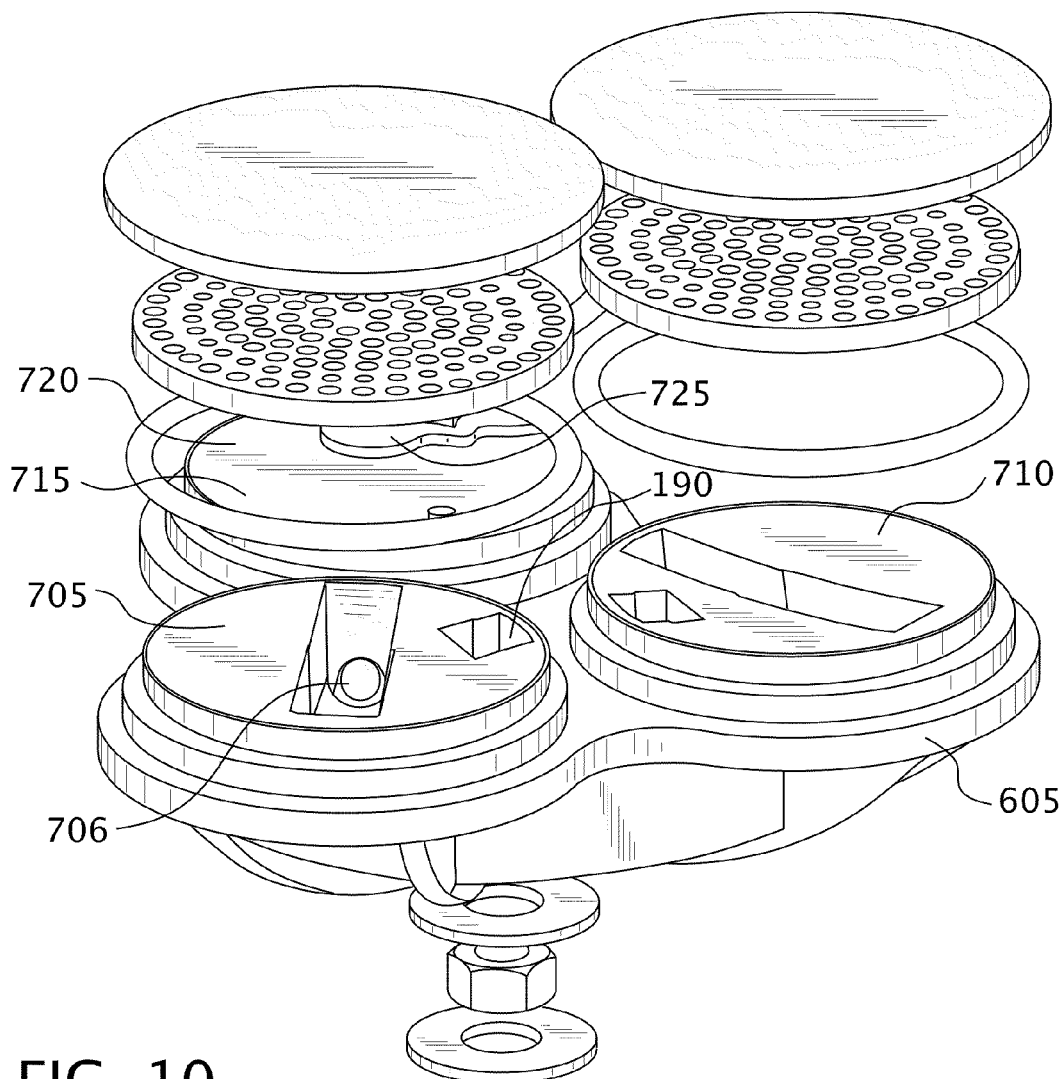
FIG. 10 is a perspective view of end cover for communicating fluid flow within the pressure swing adsorption system of FIGS. 5A and 5B according to the principles of the present invention.

FIG. 10 is a top perspective view of end cover 605 for communicating fluid flow within pressure swing adsorption system 100 according to an embodiment of the present invention. End cover 605 controls the flow between the respective sieve chambers, 130 and 135, during the desorption cycle and also controls the delivery of product gas from the respective sieve chambers, 130 and 135, to product tank 140. The perspective of end cover assembly 215 shown in FIG. 10 illustrates the conduits contained within end cover 605. The conduits in end cover 605 eliminate the need for tubing or other devices to be used to connect the chambers of pressure swing adsorption system 100. As a result, the overall weight of the pressure swing adsorption system can be reduced by the elimination of these unnecessary components.

In an exemplary embodiment, end cover 605 includes a first sieve chamber bottom plenum 705 that seals the bottom of first sieve chamber 130, and a second sieve chamber bottom plenum 710 that seals the bottom of second sieve chamber 135. Furthermore, end cover 605 includes a product tank bottom plenum 715 that seals the bottom of product tank 140. The conduits in end cover 605 allow for gas to flow from sieve chambers, 130 and 135, to product tank 140 and between sieve chambers, 130 and 135. As shown in FIG. 10, a product gas outlet port 706 provides a conduit from first sieve chamber 130 to product tank 140. A similar port, not visible in FIG. 10, provides a conduit from second sieve chamber 135 to the product tank.

The delivery of product gas to product tank 140 from the respective sieve chambers is controlled by a delivery system 720, which includes the product gas outlet ports from both sieve chambers. These product gas outlet ports terminate in product tank bottom plenum 715 and permit the delivery of concentrated oxygen from the respective sieve chambers to the product tank. Delivery system 720 can also include a dual check valve 725. This dual check valve 725 can overlie the product gas outlet ports in the product tank bottom plenum 715. Dual check valve 725 can provide a check valve 141 for product gas delivered from the first sieve chamber 130 and a check valve 142 for product gas delivered from the second sieve chamber 135. Dual check valve 725 can maintain pressure on the gas outlet ports, preventing a backflow of product gas to the respective sieve chambers.

Those of skill in the art will appreciate that the components of the various embodiments of pressure swing adsorption system 100 can be altered and modified in numerous ways without detracting from the scope of the invention. In non-limiting example, pressure swing adsorption system 100 can provide more than two sieve chambers or multiple bi-directional valves instead of multipurpose valve.

Table 2 below provides a synopsis of the specifications for two exemplary embodiments of the pressure swing adsorption system 100:

TABLE 2

| Specification | Domestic Embodiment | International Embodiment |
|---|---|---|
| Liter Flow | 0.5-5 LPM | 0.5-5 LPM |
| Sound | <45 dBA | <43 dBA |
| Oxygen Purity (at 5 Lpm) | 92% +/− 4% | 93% +/− 3% |
| Weight | 13-14 kg (28.6-30.8 Lbs) | 15-16 kg (33-35 lbs) |
| Dimensions | 580 mm (22.8") × 380 mm (15") × 240 mm (9.5") (h × w × d) | 580 mm (22.8") × 380 mm (15") × 240 mm (9.5") (h × w × d) |
| Volume | 53 liters (1.88 cu. ft.) | 53 liters (1.88 cu. ft.) |
| Oxygen Alarm Levels | Low Oxygen: 82% | Low Oxygen: 82% |
|  | Very Low Oxygen 70% | Very Low Oxygen 70% |
| Oxygen Sensing Option | Oxygen Sensor Optional | Oxygen Sensor Optional |
| Power Consumption | 360 Watts | 280-295 Watts |
| Power Cords | NEMA (US and Canada) | Unpolarized NEMA, Schuko, AS3112, or CE123 |

The specifications in the above table illustrate the overall lightweight, highly efficient, quiet operation of the pressure swing adsorption system 100. For example, and without limitation, the domestic embodiment of the pressure swing adsorption system 100 is capable of generating 5 LPM of oxygen at 90% or above purity, while only consuming 360 watts of power and creating less than 45 dBA of noise. In an additional non-limiting example, the international embodiment of the pressure swing adsorption system 100 is capable of generating 5 LPM of oxygen at 90% or above purity, while only consuming 280-295 watts of power and creating less than 43 dBA of noise.

As shown in FIG. 10, a purge control device 190 is located between the abutting surfaces of first sieve chamber bottom plenum 705 and second sieve chamber bottom plenum 710. As previously provided, purge control device 190 can be a passive orifice or an active valve capable of being controlled by logic control device 150. In those embodiments in which purge control device 190 is a passive orifice element, the orifice is usually a fixed machined orifice. This fixed orifice can be used to control the purge flow of product gas from first sieve chamber 130 to second sieve chamber 135 during the adsorption step of the pressure swing adsorption cycle. In these embodiments, the depressurization gas from one sieve chamber can be used to desorb residual nitrogen and other non product gases contained within the molecular sieve material and aid the evacuation phase of the pressure swing adsorption cycle. In this manner, the adsorption phase of one sieve chamber is used to more effectively purge the molecular sieve material of another sieve chamber.

Significantly, some embodiments of pressure swing adsorption system 100 have an active purge control device 190. In some such embodiments, active purge control device 190 can be a bi-directional solenoid valve, which is oxygen compatible and has an operational pressure range between 10 to 30 psi. Those of skill in the art will appreciate that the specific characteristics of active purge control device 190 can be altered for a particular system or desired result without detracting from the scope of the invention. Active purge control device 190 can be configured to be controlled by logic control device 150. As previously mentioned, the logic control device may include a microprocessor on a printed circuit board or other suitable logic control mechanisms. Active purge control device 190 is capable of altering the flow of purge gases between the sieve chambers in accordance with predetermined parameters corresponding to the various phases of the pressure swing adsorption cycle. Accordingly, active purge control device 190 can allow for controlled manipulation of the transfer of pressurized gas from one sieve chamber to other.

Figure 11:
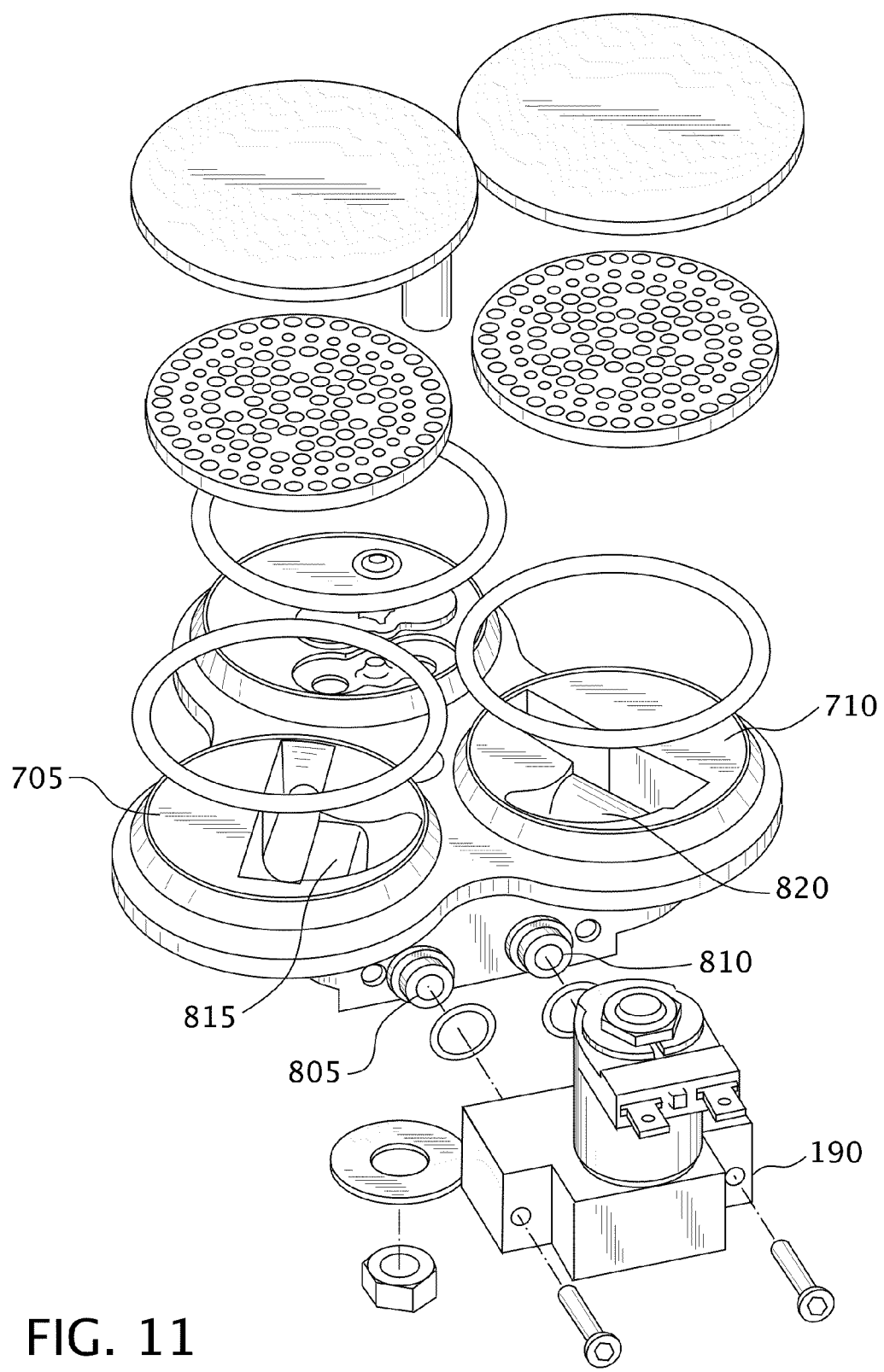
FIG. 11 is a perspective view of the end cover of FIG. 10 including an active purge control device for communicating fluid flow within the pressure swing adsorption system of the present invention.

FIG. 11 is a perspective view of end cover 605 including an active purge control device 190 for communicating fluid flow within a pressure swing adsorption system 100 according to an embodiment of the present invention. In the exemplary embodiment depicted in FIG. 11, the active purge control device 190 is a 2-way valve connected to end cover 605. The end cover 605 contains a first purge port 805 and a second purge port 810. The purge ports 805 and 810 connect to conduits contained in the sieve chamber bottom plenums. As shown in FIG. 11, a first sieve chamber conduit 815 is located in the first sieve chamber bottom plenum 705. First sieve chamber conduit 815 permits the flow of gas from the first sieve chamber 130 into the first purge port 805. Likewise, a second sieve chamber conduit 820 is located in the second sieve chamber bottom plenum 710 and is connected to the second purge port 810. Thereby, in an exemplary embodiment, gas is permitted to flow between the first sieve chamber 130 and the second sieve chamber 135 through the purge control device 190. As shown in the exemplary embodiment depicted in FIG. 11, the purge control device 190 can be positioned at the bottom of the sieve chambers 130 and 135, such that the gas flowing between the sieve chamber 130 and 135 is product gas.

In the exemplary embodiment depicted in FIG. 11, active purge control device 190 is connected to logic control device 150. In a non-limiting example, the active purge control device 190 includes solenoids that are driven by logic control device 150. In this embodiment, logic control device 150 is capable of controlling the flow of gas from first sieve chamber 130 to second sieve chamber 135. In an exemplary embodiment, logic control device 150 can control the operation of purge control device 190 in accordance with a predetermined pressure swing adsorption cycle. Additionally, the logic control device can be enabled to alter the operation of the purge control device in accordance with changes in the flow rate of the pressure swing adsorption system as calculated by the logic control device.

The controlled management of active purge control device 190 overcomes many deficiencies in conventional systems as it can have many highly desired effects on the operating characteristics and output of pressure swing adsorption system 100. In an exemplary embodiment, active purge control device 190 can be operated in an increased oxygen mode, which increases the purity of the oxygen produced by the pressure swing adsorption system. In an alternative embodiment, the active purge control device can be operated in a power conservation mode that decreases the power consumed by the pressure swing adsorption system. In a further embodiment, the active purge control device can be operated in a sound reduction mode These modes of operating the active purge control device and techniques for switching between these various modes are discussed below.

A. Increased Oxygen Mode

Controlled operation of purge control device 190 enables an increase in the oxygen concentration of the product gas produced by pressure swing adsorption system 100. Existing devices simply use a fixed machined orifice to control the purge flow of oxygen from one sieve chamber to another during the feed step of the pressure swing adsorption cycle.

Conventionally, oxygen concentrators have attempted to increase the oxygen concentration of a pressure swing adsorption system by increasing the stroke and/or bore of the compressor. Increasing the stroke and/or bore of the compressor in the system increases the pressure in the system, which may or may not increase the oxygen concentration in the product gas. Not only is this method largely ineffective, it requires more power and degrades the operating parameters of the pressure swing adsorption system thereby decreasing the lifespan of the system. Putting an increased demand on the compressor increases the amount of noise generated by the system, the amount of heat generated by the system, and the amount of power consumed by the system. All of these factors decrease the overall useable life of the system. Use of active purge control device 190, however, does not require an increase in the stroke and/or bore of the compressor to increase the pressure in the sieve chamber and concentration of oxygen in the product gas.

Active purge control device 190 contributes to increasing output oxygen concentration at lower flow rates, in comparison to prior art devices, by assisting in the desorption of non-product gases from the sieve chamber being purged and by assisting in the adsorption of the sieve chamber being fed by providing increased overall pressure levels. In a non-limiting example of the operation of pressure swing adsorption system 100 at low flow rate, first sieve chamber 130 undergoes the feed step of the pressure swing adsorption cycle with a active purge control device 190 open for at least the majority of the feed step, transferring compressed gas into second sieve chamber 135, which is undergoing the purge step. The transfer of an excess of compressed gas through the open active purge control device assists in the desorption of non-product gases, such as nitrogen, from second sieve chamber 135. This enables the second sieve chamber to more efficiently separate the non-product gases from the compressed ambient air inputted during the next feed phase of second sieve chamber 135.

In another non-limiting example, a delay is inserted before the beginning of the purge step, which enables an increase in the peak pressure of the adsorption phase. In this example, the sieve chamber being fed can be quickly pressurized with purge device 190 in a closed position. Therefore, greater pressures are attained sooner and maintained for longer periods in the sieve chamber during the adsorption phase. Once the active purge delay period expires, purge device 190 can be opened and the concentrated product gas can be transferred into the sieve chamber being purged to regenerate that sieve chamber.

It can thus be appreciated that active purge control device 190 can increase oxygen concentration by inserting a delay in the beginning of the purge step of the pressure swing adsorption cycle and by transferring product gas to a sieve chamber in a desorption phase. The delay in the beginning of the purge step results in a change from the conventional pressure swing adsorption cycle. Conventionally, the feed step and the purge step of the pressure swing adsorption cycle were combined. In accordance with an exemplary embodiment of the present invention, active purge control device 190 allows for a pure feed step in which compressed ambient air is inserted into the sieve chamber without loosing any pressure due to purging. Therefore, in some embodiments, the active purge control device can be used to insert delay into the purge step in accordance with the desired output flow rate of the pressure swing adsorption system. In exemplary embodiment, the amount of delay is increased in proportion to the increase in the output flow rate of the pressure swing adsorption system. This pure feed step can be followed by a feed plus purge step in the pressure swing adsorption cycle Some embodiments of active purge control device 190 are configured with an orifice that is larger than the conventional fixed orifice. In an exemplary embodiment, active purge control device 190 has an orifice that is 30% to 50% larger than the typical fixed orifice purge device. In one embodiment, the oxygen volumetric flow rate targets for the active purge control device 190 are 18 LPM at 15 psi, 21 LPM at 20 psi, and 24 LPM at 25 psi. The larger orifice allows the pressure swing adsorption system 100 to compensate for the reduced time of the purge step. More specifically, active purge control device 190 having a larger orifice permits a greater volume of compressed concentrated product gas to exit the sieve chamber being fed and enter the sieve chamber being regenerated.

Figure 12:
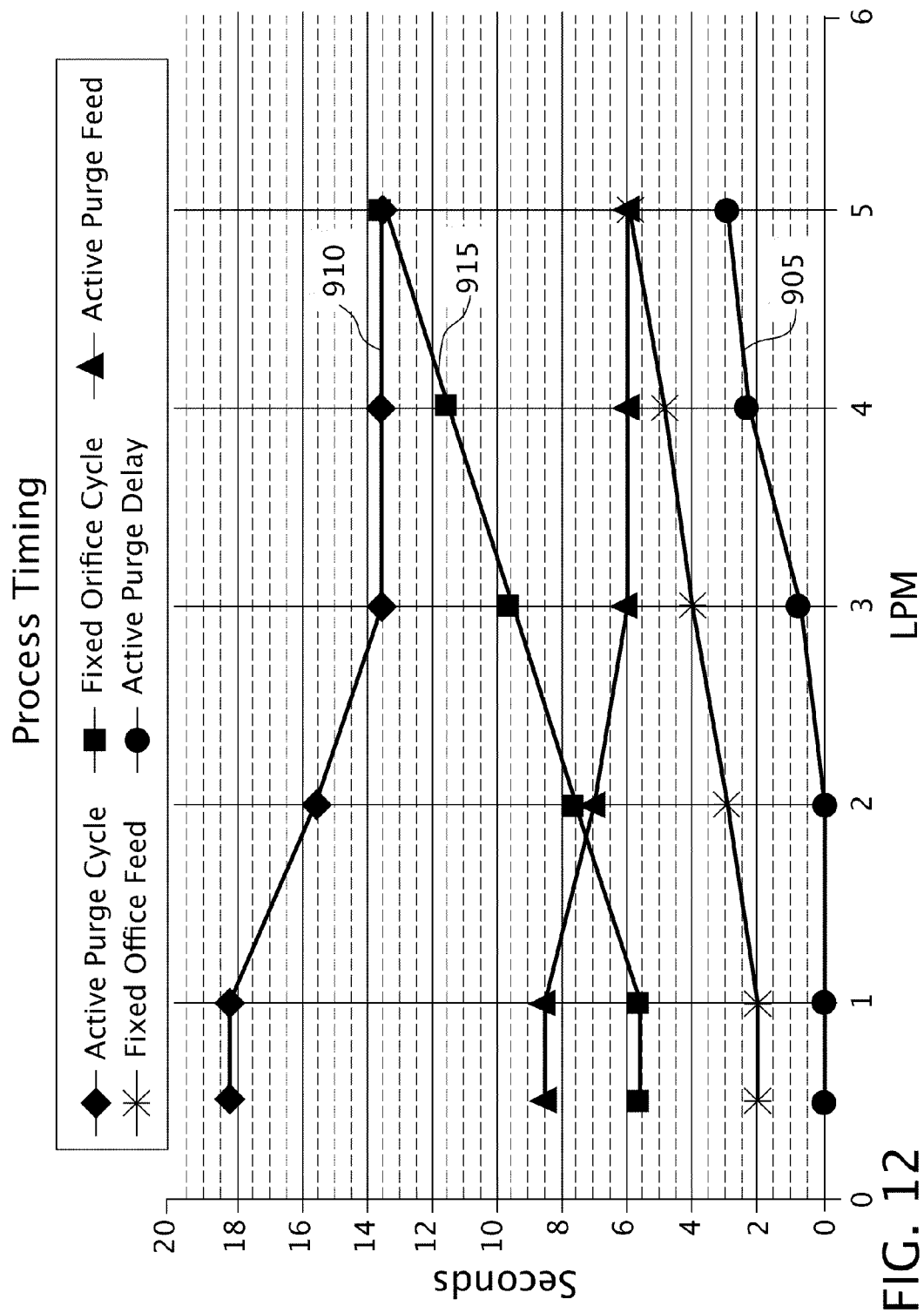
FIG. 12 is a chart of the duration of certain phases of the pressure swing adsorption cycle versus the flow rate of an embodiment of the pressure swing adsorption system according to the principles of the present invention.

FIG. 12 is a chart of the duration of certain phases of the pressure swing adsorption cycle versus the flow rate of an embodiment of the pressure swing adsorption system 100. FIG. 12 illustrates the phase durations for both an embodiment of pressure swing adsorption system 100 in which a fixed orifice purge control device 190 is implemented and also a separate embodiment in which an active purge control device 190 is implemented. As shown in FIG. 12, a data plot line 905 for the "Active Purge Delay" increases as the flow rate or LPM of the pressure swing adsorption system increases. As shown, at 0.5 LPM the "Active Purge Delay" is zero seconds and at 5 LPM the "Active Purge Delay" is 3 seconds. Therefore, the purge delay increases as the flow rate increases. Varying the "Active Purge Delay" in accordance with flow rate increases the oxygen concentration in the product gas.

Figure 13:
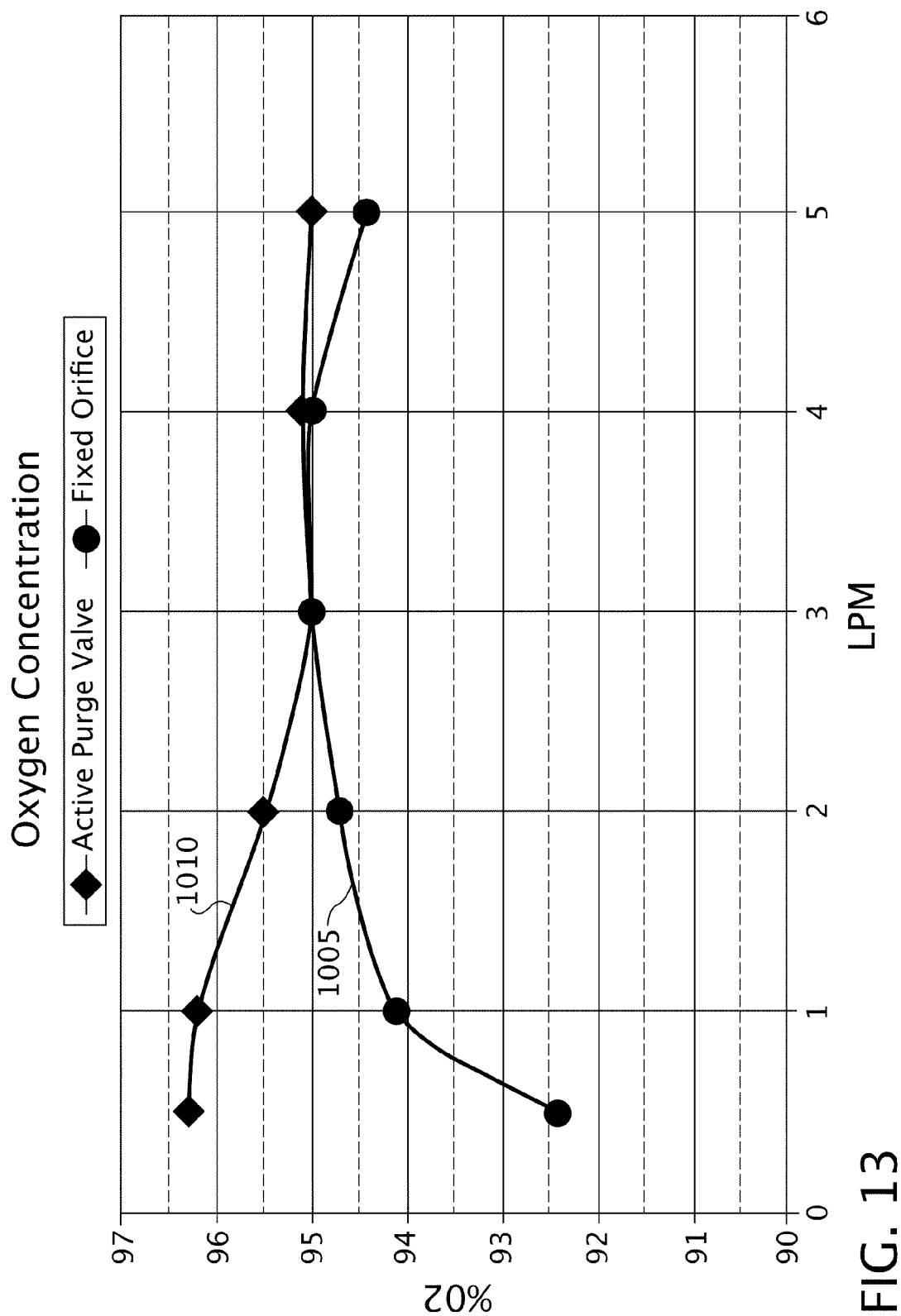
FIG. 13 is a chart of the oxygen concentration of the product gas for an embodiment of the pressure swing adsorption system according to the principles of the present invention.

FIG. 13 is a chart of the oxygen concentration of the product gas for an embodiment of pressure swing adsorption system 100. The chart illustrates the oxygen concentration of the product gas generated by an embodiment of pressure swing adsorption system in which purge control device 190 is a fixed orifice, and an embodiment in which the purge control device is active. As shown, the "Fixed Orifice" embodiment exhibits a decrease in oxygen concentration at both low flow rates and high flow rates. For example, the oxygen concentration for the "Fixed Orifice" embodiment decreases to approximately 92.4% at 0.5 LPM and similarly to approximately 94.4% at 5 LPM. The bell-shaped nature of a data plot line 1005 for the "Fixed Orifice" embodiment is corrected in the "Active Purge Valve" embodiment. As shown in FIG. 13, a data plot line 1010 for the "Active Purge Valve" embodiment is essentially a slowly descending line. Active purge control device 190 permits a more efficient pressure swing adsorption cycle in which a higher concentration of oxygen is produced. For example, the oxygen concentration for the "Active Purge Valve" embodiment at 0.5 LPM is approximately 96.4%.

Significantly, those of skill in the art will appreciate that the implementation of an exemplary embodiment of the pressure swing adsorption system in increased oxygen mode enables the production of oxygen at or above the traditional maximum valve for oxygen concentration. Conventional devices have yielded a maximum oxygen concentration of 95.6%. As shown by the data provided in FIG. 13, an exemplary embodiment of the pressure swing adsorption system in increased oxygen mode is capable of going far beyond this previous maximum oxygen concentration to levels at 96% and above. The pressure swing adsorption devices of the prior art have been unable to provide oxygen concentrated at levels higher than 95.6% in an mode of operation. Thus, pressure swing adsorption system 100 overcomes the deficiencies of the prior art and makes extraordinarily pure oxygen generation a possibility for a pressure swing adsorption system.

As data plot line 1010 for the "Active Purge Valve" embodiment shown in FIG. 13 illustrates, the oxygen concentration decreases only slightly as the flow rate increases. For the exemplary embodiment graphed in FIG. 13, the oxygen concentration is approximately 95% at the high flow rate of 5 LPM. The implementation of the active purge control device enables an overall increase in the purity of the oxygen produced by the pressure swing adsorption system.

Figure 14A:
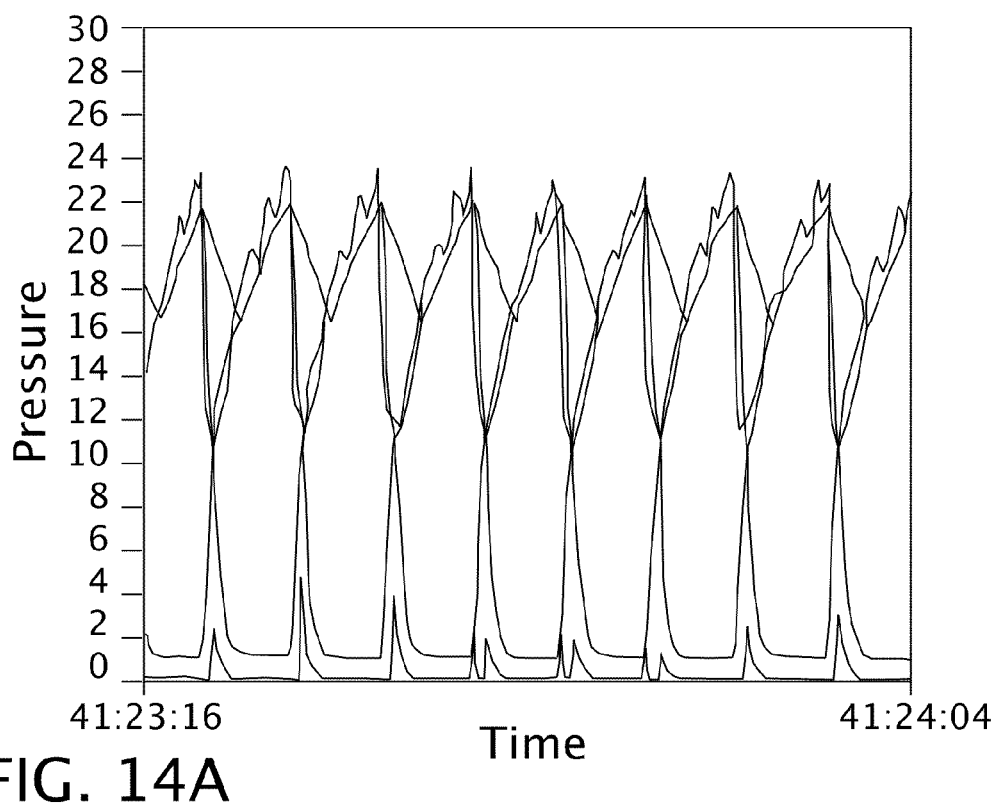
FIG. 14A is a chart of the pressure values versus time for a fixed purge device embodiment of the pressure swing adsorption system according to the principles of the present invention.
Figure 14B:
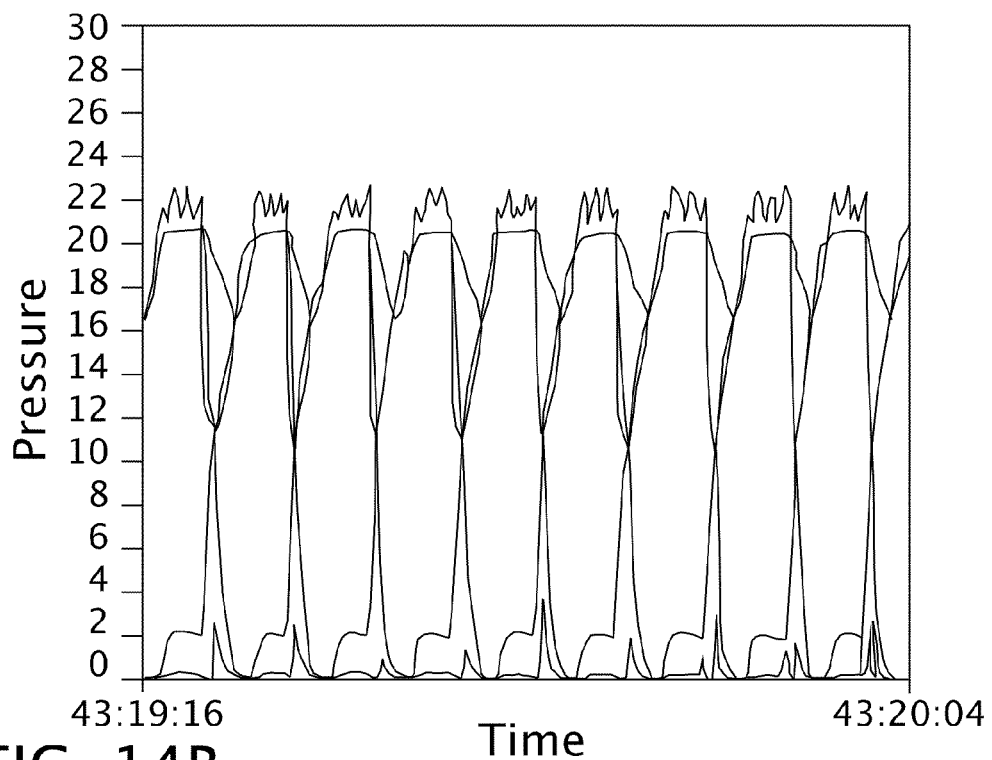
FIG. 14B is a chart of the pressure values versus time for an active purge device embodiment of the pressure swing adsorption system according to the principles of the present invention.

FIG. 14A provides a chart of the pressure values versus time for a fixed purge device embodiment of pressure swing adsorption system 100. FIG. 14B provides a chart of the pressure values versus time for an active purge device embodiment of the pressure swing adsorption system. As illustrated in the charts, the pressure value traces for the pressure swing adsorption system embodiment with the active purge control device, FIG. 14B, are more uniform (square) than the traces for the pressure swing adsorption system embodiment with the passive purge control device. FIG. 14A illustrates how the pressurization for sieve chambers with a passive purge control device occurs along a relatively gradual slope from approximately 12 psi to approximately 20 psi. Contrastingly, the pressurization for sieve chambers with an active purge control device, in which a purge delay is implemented in the pressure swing adsorption cycle, occurs quite rapidly and essentially remains constant at approximately 21 psi. Thus, higher pressures are attained sooner and maintained for longer periods during adsorption. Higher oxygen concentrations result from the more uniform nature of the pressure traces for embodiments implementing an active purge control device. In a non-limiting example, the oxygen purity for the active purge control device embodiment is 95.03% oxygen at 5 LPM compared to 94.42% oxygen at 5 LPM for the passive control device embodiment.

Another advantage provided by the active purge control device is the ability to extend the cycle time for operation at lower flow rates. An increased cycle time at lower flow rates is highly desired by users of the pressure swing adsorption systems because the sound of machine appears to be running smoother when the cycle time is increased. The association of a smoother running machine is due to the low frequency of exhaustion or desorption phases. When a pressure swing adsorption system is operating at a fast cycle time, the exhaustion device is more frequently in operation and the noise of the exhaustion device, sometimes referred to as the "blow down" muffler, is negatively associated with a rapidly working piece of equipment. The high frequency of exhaust pulses is detrimental to the perception of the operation of the device. Additionally, the high frequency of exhaust pulses places significant stress and wear and tear on the components of the system, thereby decreasing the operable life of the system.

Reverting back to FIG. 12, the chart provides data plot lines for multiple phases of the pressure swing adsorption cycle for both the pressure swing adsorption system with a passive device and an active purge device. As shown, a data plot line 910 for the "Active Purge Cycle" increases at lower flow rates and a data plot line 915 for the "Fixed Orifice Cycle" decreases at lower flow rates. In a non-limiting example, as shown by the chart data in FIG. 9, the "Active Purge Cycle" time is approximately 18 seconds at 0.5 LPM and is approximately 5.5 seconds for the "Fixed Orifice Cycle" at 0.5 LPM. Therefore, the active purge device 190 allows for longer cycle times and a smoother perception of operation and increased device lifespan.

B. Power Conservation Mode

In addition to enabling an increased oxygen concentration mode, controlled operation of purge control device 190 enables a decrease in the power consumed by pressure swing adsorption system 100. Embodiments of the pressure swing adsorption system operated in power conservation mode minimize the power consumption of the system by implementing a flow rate algorithm for the active purge control device. The flow rate algorithm for the power conservation mode of the pressure swing adsorption system varies the timing of the active purge control device from the algorithms implemented to achieve maximum oxygen concentration.

Figure 15:
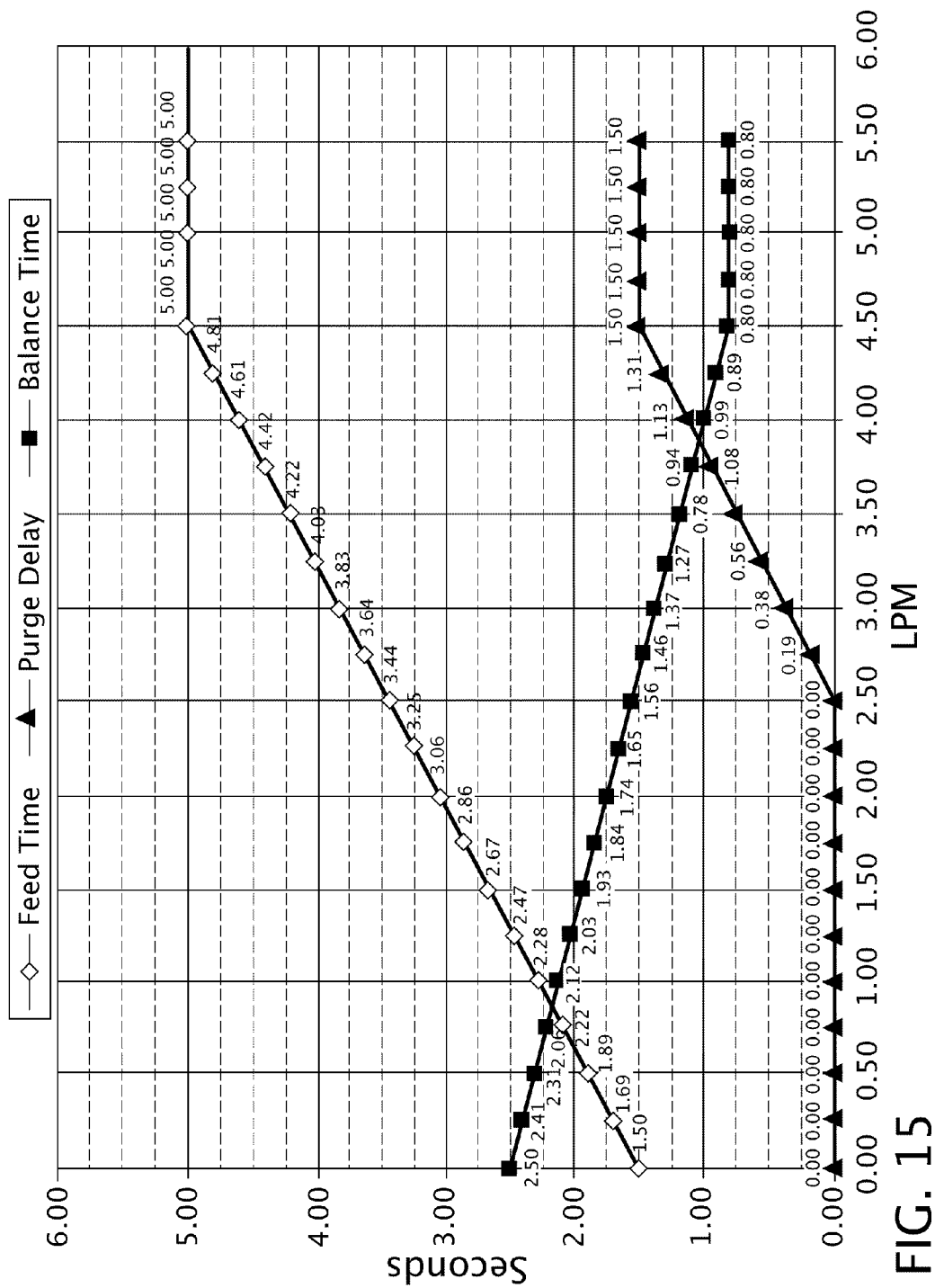
FIG. 15 is a chart of the time values for the different phases of the pressure swing adsorption cycle for an embodiment of the pressure swing adsorption system of the present invention operated in power conservation mode.

FIG. 15 provides a chart of the time values for the different phases of the pressure swing adsorption cycle for an embodiment of pressure swing adsorption system 100 operated in power conservation mode. The time values illustrated in FIG. 12 correspond to a flow rate algorithm for an exemplary embodiment of pressure swing adsorption system 100 in power conservation mode. For the exemplary embodiment of the pressure swing adsorption system shown in FIG. 15, the flow rate algorithm increases the feed time linearly up to a maximum value of 5 seconds at 4.5 LPM. The balance time, or equalization of the sieve chambers, decreases linearly to a minimum value of 0.8 seconds at 4.5 LPM. The purge delay for the active purge control device is held at zero for flow rates at or below 2.5 LPM and increases linearly for flow rates between 2.5 LPM and 4.5 LPM. The implementation of the flow rate algorithm corresponding to data provided in FIG. 12 results in a lower power consumption by the pressure swing adsorption system.

Figure 16:
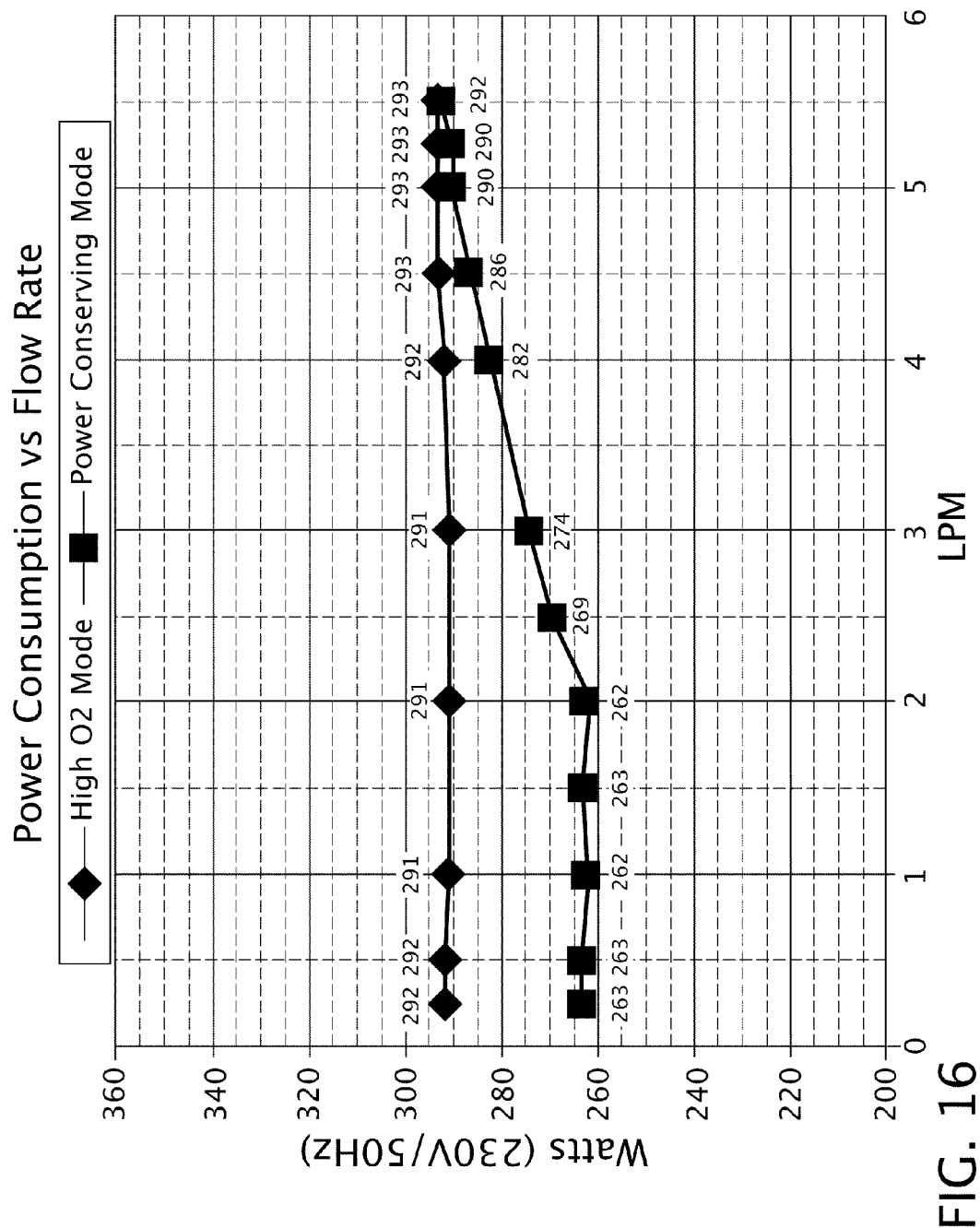
FIG. 16 is a chart of the power consumption of an embodiment of the pressure swing adsorption system of the present invention operated in power conservation mode.

FIG. 16 provides a chart of the power consumption of an embodiment of pressure swing adsorption system 100 operated in power conservation mode. As illustrated, the implementation of a power conservation flow rate algorithm for active purge control device 190 results in a significant decrease in the power consumed by the device. In a non-limiting example, the power consumed by an exemplary embodiment of the pressure swing adsorption system at 1 LPM in power conservation mode is approximately 30 Watts less than an embodiment of the pressure swing adsorption system at 1 LPM in increased oxygen mode. The decrease in power consumption provided by intelligent management of the active purge control device provides many significant advantages, in addition to the power consumption savings for the pressure swing adsorption system. The reduction in power also leads to a reduction in the pressures maintained in the pressure swing adsorption system during the pressure swing adsorption cycle. This reduction in pressure decreases the stress applied upon the system by operation. Furthermore, the decreased pressures, in accordance with the ideal gas law, lead to a decrease in operating temperature. This reduction in temperature servers to further alleviate the stress applied to the system by operation. Significantly, the reduction in power, pressure, and temperature result in a longer operable for the pressure swing adsorption system.

Figure 17:
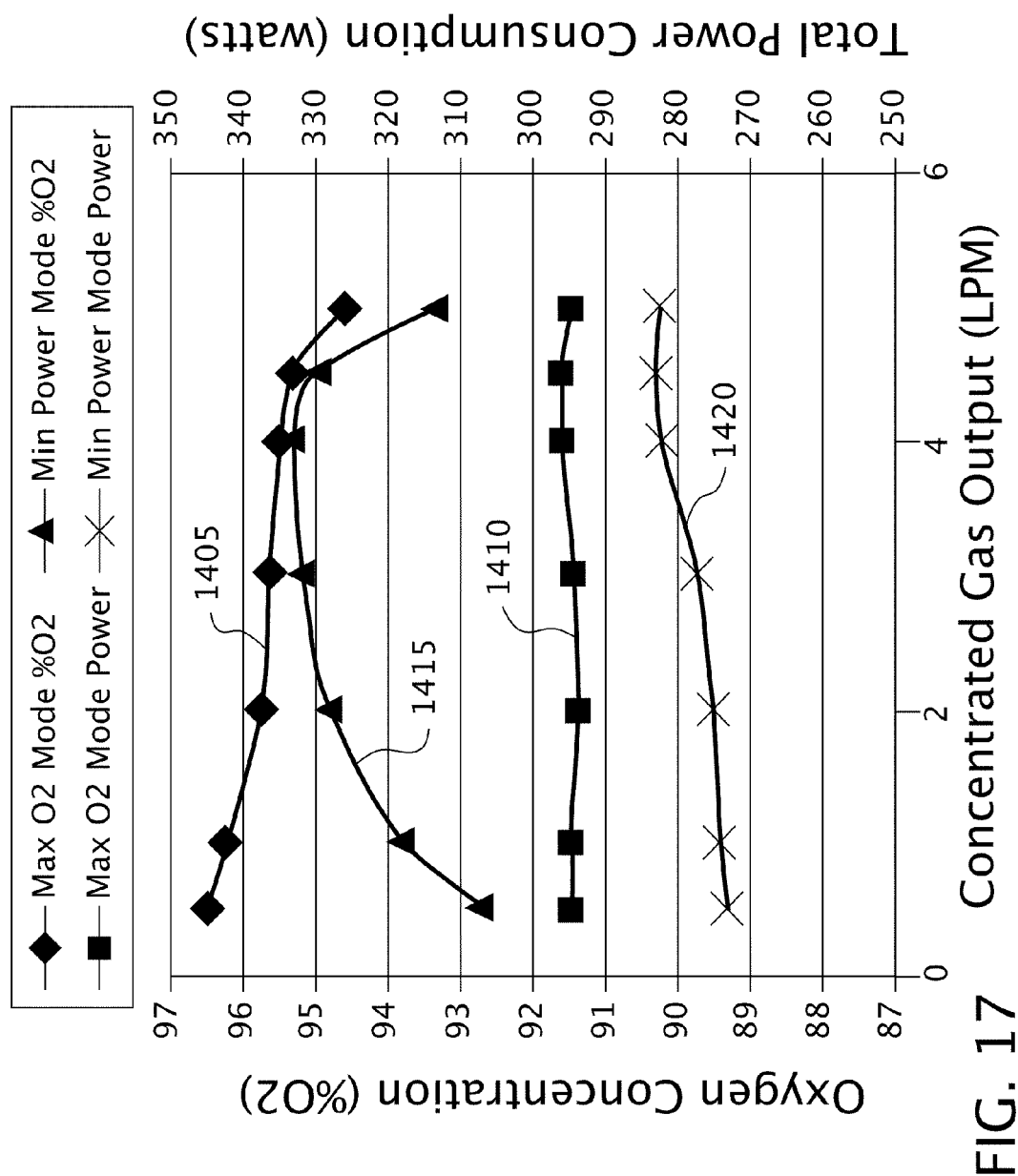
FIG. 17 is a chart of the oxygen concentrations of the product gas and power consumptions by various embodiments of the pressure swing adsorption system according to the principles of the present invention.

FIG. 17 is a chart of the oxygen concentrations of the product gas and power consumptions of an embodiment of pressure swing adsorption system 100 operating in various modes. In accordance with an exemplary embodiment of the present invention, the same pressure swing adsorption system can be operated in either an increased oxygen mode or a power conservation mode by varying the operation of active purge control device 190. More specifically, altering the pressure swing adsorption cycle by use of the active purge control device can allow the same system to operate in either increased oxygen mode or power conservation mode.

In an exemplary embodiment, the pressure swing adsorption system can be switched from increased oxygen mode to power conservation mode by logic control device 150. In an exemplary embodiment, an instruction can be sent to the logic control device to change the operation of the active purge control device in accordance with increase oxygen mode operation or power conservation mode operation. In an exemplary embodiment, the user can access a user interface on the pressure swing adsorption system to instruct the logic control device to operate in a desired mode. In an alternative embodiment, the instruction sent to the logic control device is caused by flipping a switch on the pressure swing adsorption system. Those of skill in the art will appreciate that the method by which the pressure swing adsorption system is switched from mode to mode can vary without detracting from the scope of the invention.

As shown by a data plot line 1405 in FIG. 17, operation of pressure swing adsorption system 100 in increased oxygen mode results in an higher than normal oxygen concentration output for the entire range of flow rates from 0.5 LPM to 5 LPM. Although the oxygen concentration is improved in increased oxygen mode, the power consumption of pressure swing adsorption system 100, as shown by a data plot line 1410, is comparable to conventional devices. When the oxygen concentration is of primary importance, pressure swing adsorption system 100 can be operated in increased oxygen mode. On the other hand, when power consumption is of primary importance, the same pressure swing adsorption system can be switched to be operated in power conservation mode. As shown by a data plot line 1420 in FIG. 17, the power consumed by the pressure swing adsorption system is minimal when operated in power conservation mode. The oxygen concentration produced during power conservation mode, however, is more comparable to conventional systems, as shown by the bell curved nature of data plot line 1415 in FIG. 17. Therefore, the pressure swing adsorption system can be operated according to the patients' demands.

C. Sound Reduction Mode

In addition to enabling an increased oxygen concentration mode and power conservation mode, the present invention contemplates controlling the operation of purge control device 190 so that pressure swing adsorption system 100 operates in a sound reduction mode. Embodiments of the pressure swing adsorption system operated in sound reduction mode minimize the sound of the system by implementing a flow rate algorithm for the active purge control device. The flow rate algorithm for the sound reduction mode of the pressure swing adsorption system varies the timing of the active purge control device from the algorithms implemented to achieve either maximum oxygen concentration or minimum power consumption.

The sound level of an oxygen concentrator system comprises sounds of both a constant and a cyclical nature. Examples of constant sounds are noise from compressor 115 and a cooling fan (not shown). These components are running and producing an essentially constant noise during the operation of the system. Cyclical sounds occur on top of or in addition to the constant noises. These include the noise of valves 120 and 190 switching states, and the noise of the waste gas exiting the exhaust muffler 125. It is the sounds associated with valves 120 and 190 switching state and the sound emanating from exhaust muffler 125 that the sound reduction mode aims to minimize.

This is accomplished first by examining when purge valve device 190 needs to cycle from off to on, and where it can be in only one state (on or open) thereby not making any noise to due changing states from off to on and back again. Whereas in the increased oxygen mode, the purge valve device is actively changing states and, thus, making noise at all oxygen output flow rates. In the sound reduction mode, on the other hand, purge valve device 190 is cycled only in flow rates above 3 LPM. Below 3 LPM, the valve is held open throughout the PSA cycle, effectively creating a permanent, relatively large orifice through which the oxygen purge gas can pass effectively for those flow rates, i.e., rates <3 LPM. Above 3 LPM, the purge valve operates as described above in the increased oxygen mode, whereby the valve is held closed for a brief period to quickly build pressure in sieve bed, then opened to begin the purge step.

At the same time, valve 120 is operated in a manner whereby it has essentially the same on/off timing at all oxygen output flow rates. This is in contrast to the power conservation mode, where valve 120 is cycled at a progressively faster rate as the flow rate decreases. While the increased oxygen mode extends the cycling frequency of valve 120 even further than the sound reduction mode, the increased oxygen mode produces higher pressures, which in turn lead to higher exhaust "blow-down" noise from muffler 125.

Figure 18:
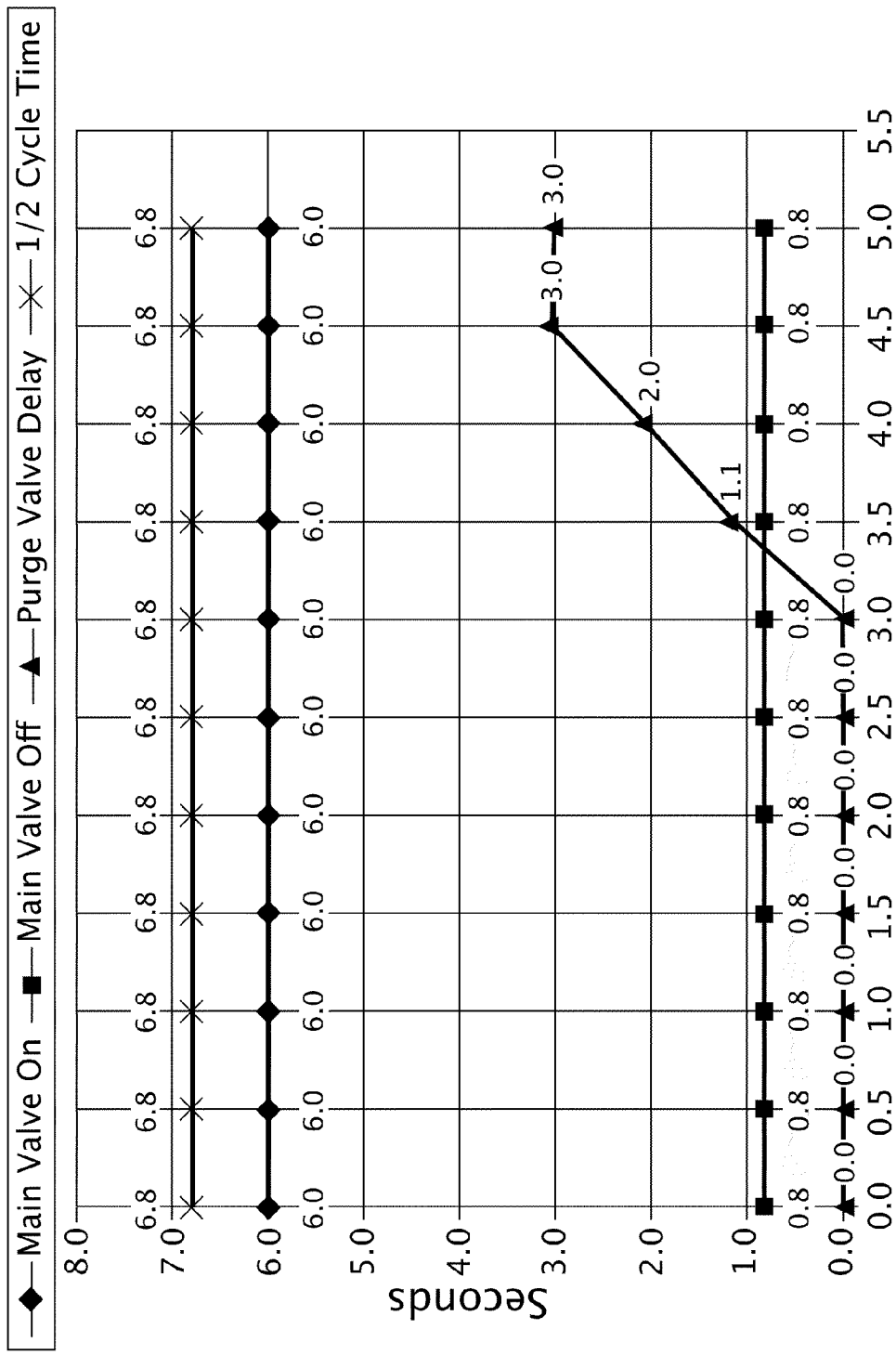
FIG. 18 is a valve time chart for a sound reduction mode according to the principles of the present invention.

FIG. 18 describes an example of the specific valve timing that can be used to achieve the sound reduction mode using pressure swing adsorption system 100 according to the principles of the present invention. The sound level due to exhaust gases passing through exhaust muffler 125 is directly related to the system pressure upstream of the muffler just before valve 120 switches and dumps the purged bed pressure through exhaust muffler 125. The system pressure at this point in the cycle is called the "balance pressure", because valve 120 allows communication between both sieve beds and the compressor for just enough time to bring the sieve beds to the same pressure point. The balance pressure is higher in the increased oxygen mode and lower in the sound reduction mode. As a result, the peak muffler pressure and peak sound level due to the muffler are lower in the sound reduction mode.

Figure 19:
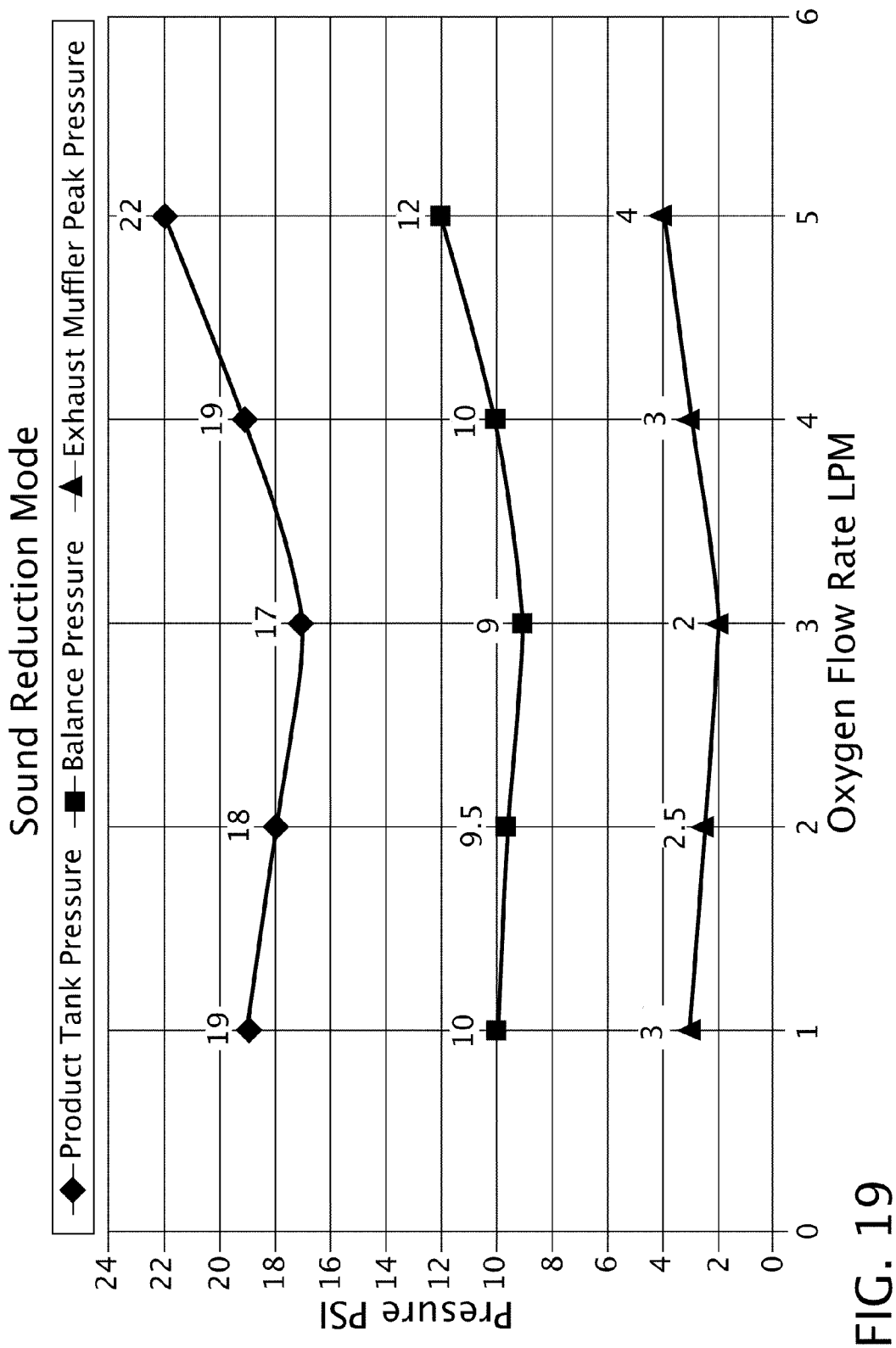
FIG. 19 is a chart illustrating peak pressures of various components of the PSA system when the system is operating in a sound reduction mode.
Figure 20:
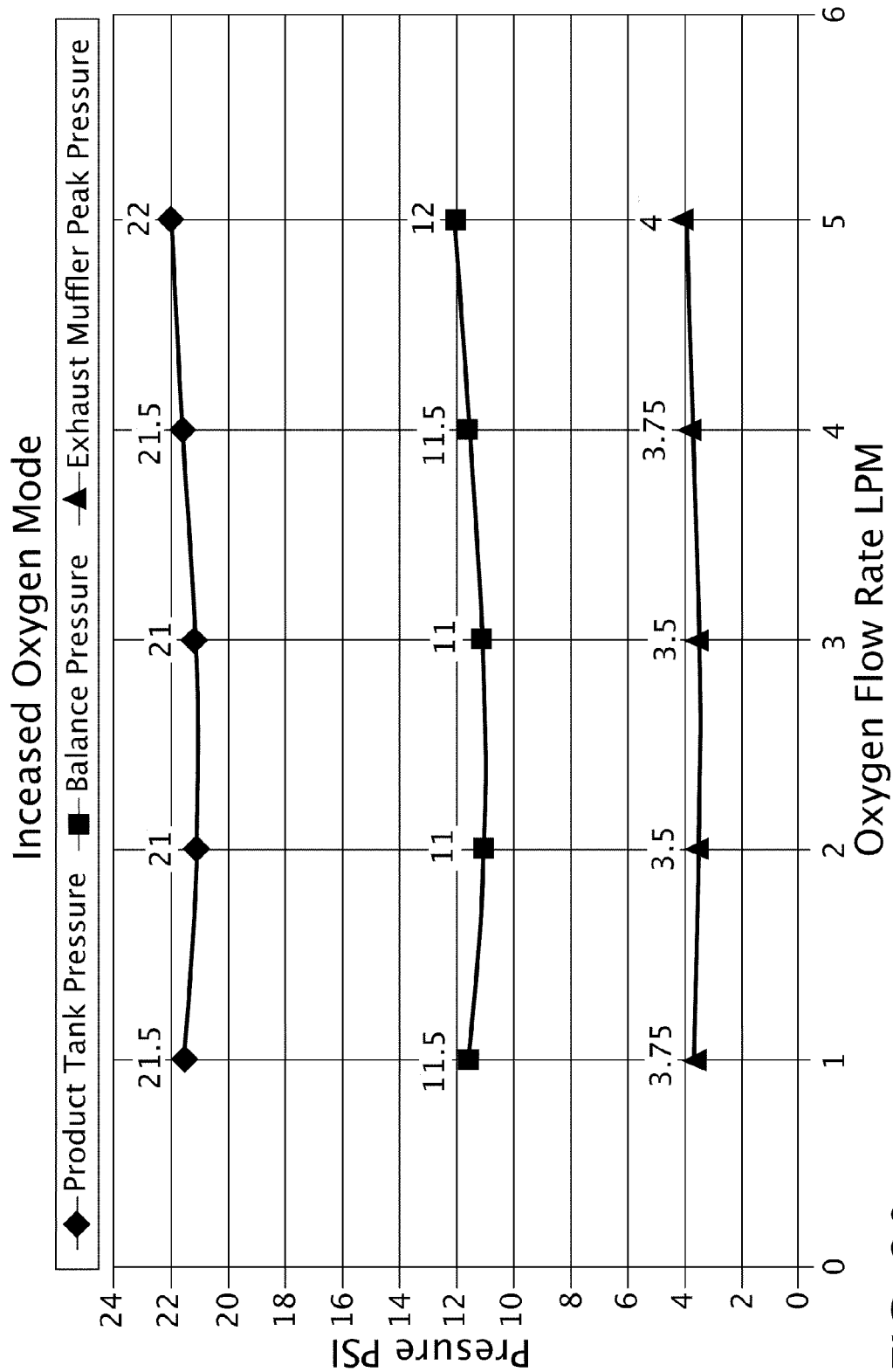
FIG. 20 is a chart illustrating peak pressures of various components of the PSA system when the system is operating in an increased oxygen mode.

FIG. 19 illustrates a typical product tank pressure 600*a*, system balance pressure 601*a*, and exhaust muffler peak pressure 602*a*, for the sound reduction mode, and FIG. 20 illustrates a typical product tank pressure 600*b*, system balance pressure 601*b*, and exhaust muffler peak pressure 602*b*, for the increased oxygen mode. It can be appreciated from comparing FIGS. 19 and 20 that the difference between these two modes is especially apparent at 1-3 LPM flow rates, which are the most common flow rates used in a 5 LPM max flow rate oxygen concentration system.

The benefit of the lower peak muffler pressures is demonstrated by measuring the maximum sound level of the system when operated in both the increased oxygen mode and the sound reduction mode. At 3 LPM, the peak sound level of a typical system operating in the sound reduction mode was registered at 45.7 dBA, while the same system operating in the increased oxygen mode registered a peak noise level of 47.3, under the same test conditions.

D. Switching Between Modes

The present invention contemplates that the selection of the operating mode for the pressure support system can be done manually or automatically. For manually selecting the operating mode, an input/output device 180 is provided that communicates with logic control device 150. The user can manually select the operating mode, e.g., the increased oxygen mode, power conservation mode, sound reduction mode using input/output device 180. The present invention contemplates that input/output device 180 is any device suitable for allowing this function, such as switches, knobs, buttons, keypad, touch screen displays, and a voice activated or speech recognition device. This provides the user with a wide degree of freedom in selecting how best to operate the PSA system according to the current needs of the user.

As noted above, the present invention also contemplates automatically causing the system to switch between mode. In an exemplary embodiment, the system normally operates in the power conservation mode as the default mode. However, if oxygen sensor 165 detects that system performance in terms of the purity of the oxygen output has deteriorated by a certain amount or fallen below a threshold value, the system can automatically switch from the current operating mode (power consumption mode or noise reduction mode) to the increased oxygen mode. Similarly, the present invention contemplates monitoring the power consumption of the system and/or the sound of the ambient environment and switching to the power consumption and/or the noise reduction modes based on the result of such monitoring. The present invention further contemplates monitoring the oxygen concentration of the system and gradually and automatically moving towards either the power conservation or sound reduction mode as long as the oxygen concentration stays above a threshold limit, e.g. 90%.

E. Extended Balance

Typically the pressure swing adsorption cycle incorporates a balance phase. In this balance phase, the sieve chambers of the pressure swing adsorption system can be equalized. The balance phase is relied upon to utilize the pressurization of one sieve chamber to aid in pressurizing another sieve chamber and thereby decrease the demands placed upon the compressor. After a sieve chamber completes a purge phase, the pressure in the sieve chamber is depleted. To have an effective subsequent feed phase, the sieve chamber must be repressurized. In pressure swing adsorption systems with more than one sieve chamber, the purge and feed phases can be synchronized such that when one sieve chamber is in the purge phase, its counterpart is in the feed phase. Thus, the chamber being purged can be used to help pressurize the chamber being fed. The balance phase occurs between the feed phase and the purge phase.

Conventionally, as described in U.S. Pat. No. 5,183,483, the balance phase involves opening the both the sieve chamber ports and the supply input port such that compressed air can flow into the sieve chamber to be pressurized from both the compressor and the pressurized sieve chamber. In an exemplary embodiment, the valve used is an SMC valve with pilot operated solenoid devices capable of switching at a minimum pressure. Typically, once the pressure between the sieve chambers has equalized, the sieve chamber port is closed.

In an exemplary embodiment of pressure swing adsorption system 100, contrary to the techniques used in conventional devices, the balance phase of the pressure swing adsorption cycle can be extended beyond the time at which the sieve chambers reach equal pressures. In one embodiment, once first sieve chamber 130 and second sieve chamber 135 reach equal pressure, both ports 122 and 123 to the sieve chambers can remain open to supply input port 142 from compressor 115 and thereby increase the pressure in both sieve chambers 130 and 135.

The implementation of an extended balance phase in the pressure swing adsorption cycle has many significant advantages. Increasing the balance time permits an increase in the cycle time of pressure swing adsorption cycle. This increase in cycle time decreases the frequencies of pulses between the operation of pressure swing adsorption system 100. Notably, the lengthened cycle time decreases the frequency of the operation of exhaust device 125, and thereby decreases the noise generated by the device over time. Additionally, the extended balance phase raises the valve switching pressures within the system. In a non-limiting example, the minimum specification threshold for the switching pressure may be 7 psi, and switching can typically occur at or slightly above this threshold in prior art machines. The extended balance phase in an exemplary embodiment of pressure swing adsorption system 100 increases the overall pressure such that average switching pressure can preferably be in the range of 10 to 13 psi. Therefore, the extended balance can be used to divide the compressed gas input from compressor 115 among the two sieve chambers 130 and 135. Splitting the compressed gas input results in a decrease in the overall amount of compressed gas inputted into the sieve chamber undergoing the adsorption phase of the pressure swing adsorption cycle. In this manner, the extended balance phase can increase the oxygen concentration levels at low flow rates.

Figure 21:
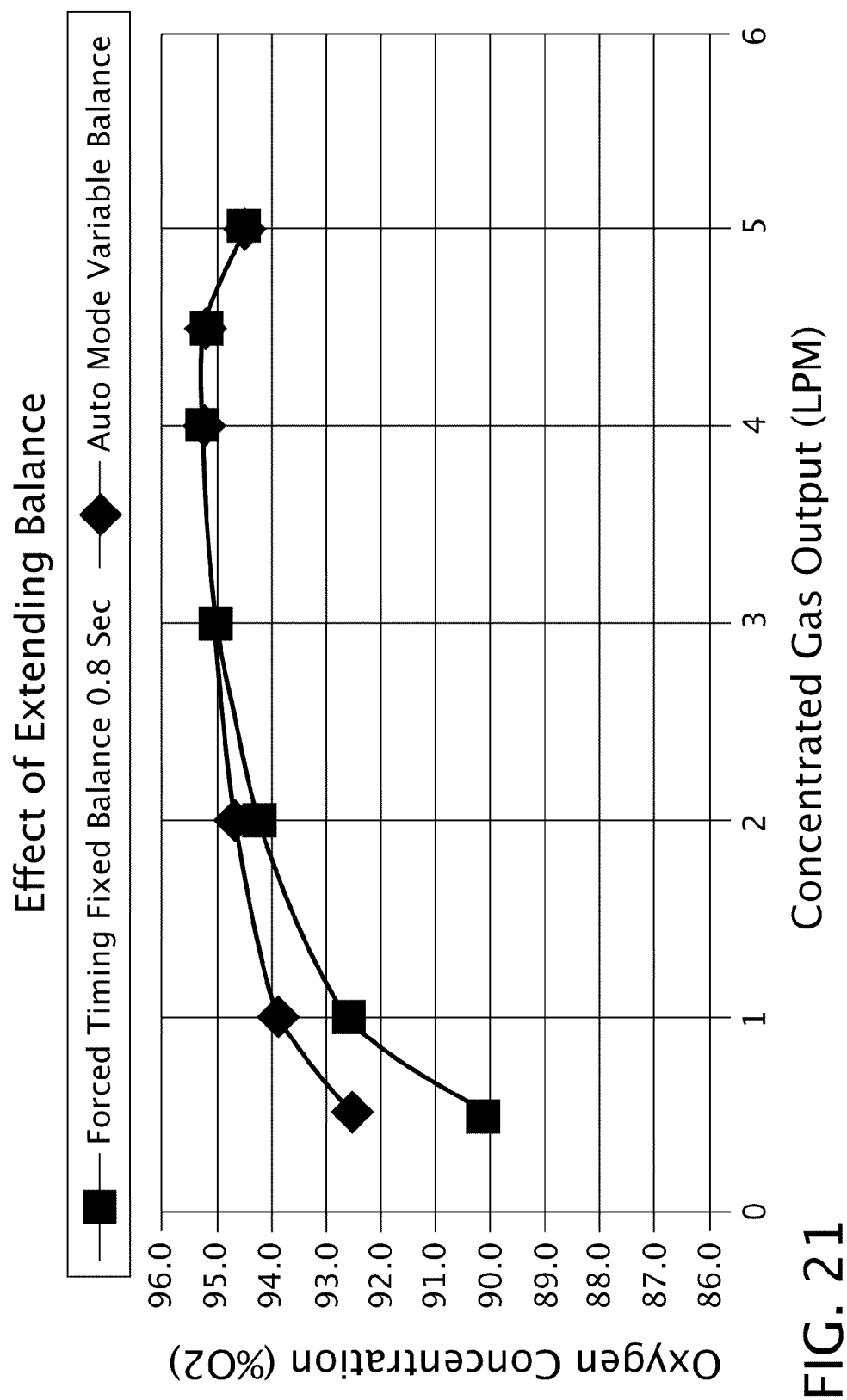
FIG. 21 is a chart illustrating the effect on oxygen concentration of operation of the pressure swing adsorption system of the present invention in extended balance mode.

FIG. 21 provides a chart illustrating the effect on oxygen concentration of operation of pressure swing adsorption system 100 in extended balance mode. The chart of FIG. 15 provides oxygen concentrations generated by a system operating under a traditional pressure swing adsorption cycle and the oxygen concentration for a system operating under an extended balance mode of a pressure swing adsorption cycle in accordance with an embodiment of the present invention. As shown in the FIG. 21, adjusting the pressure swing adsorption cycle of the pressure swing adsorption system to operate in extended balance mode greatly increases the oxygen concentration of the product gas produced. In an non-limiting example, the system in traditional mode generates 90.1% oxygen at 0.5 LPM and the system in extended balance mode generates 92.6% oxygen at 0.5 LPM. Moreover, the oxygen concentration produced by the system in extended balance mode is greater than the system operating in the traditional mode for the range of flow rates from 0.5 LPM to 3 LPM.

Adjusting the pressure swing adsorption cycle of pressure swing adsorption system 100 to operate in an extended balance mode in accordance with an embodiment of the present invention overcomes many deficiencies in the prior art. The traditional approach for raising oxygen concentrations requires the cycle time to be fixed and the feed time, or adsorption phase, to be increased. The traditional approach may or may not be successfully in slightly increasing the oxygen concentration of the product gas. The detriment to the operation of the system, however, is quite significant. Increasing the feed time, increases the overall pressures within the system. The increases in overall pressures, increases the load on the compressor and thus the power consumed by the system. Not only is more power consumed, the increase in pressures within the system applies more stress to system and decreases the operable life of the system. Operation of pressure swing adsorption system 100 in extended balance mode actually increases the oxygen concentration while also increasing the cycle time. Thus, the stress on the system is decreased and the operable life of the system 100 can be lengthened.

Figure 22:
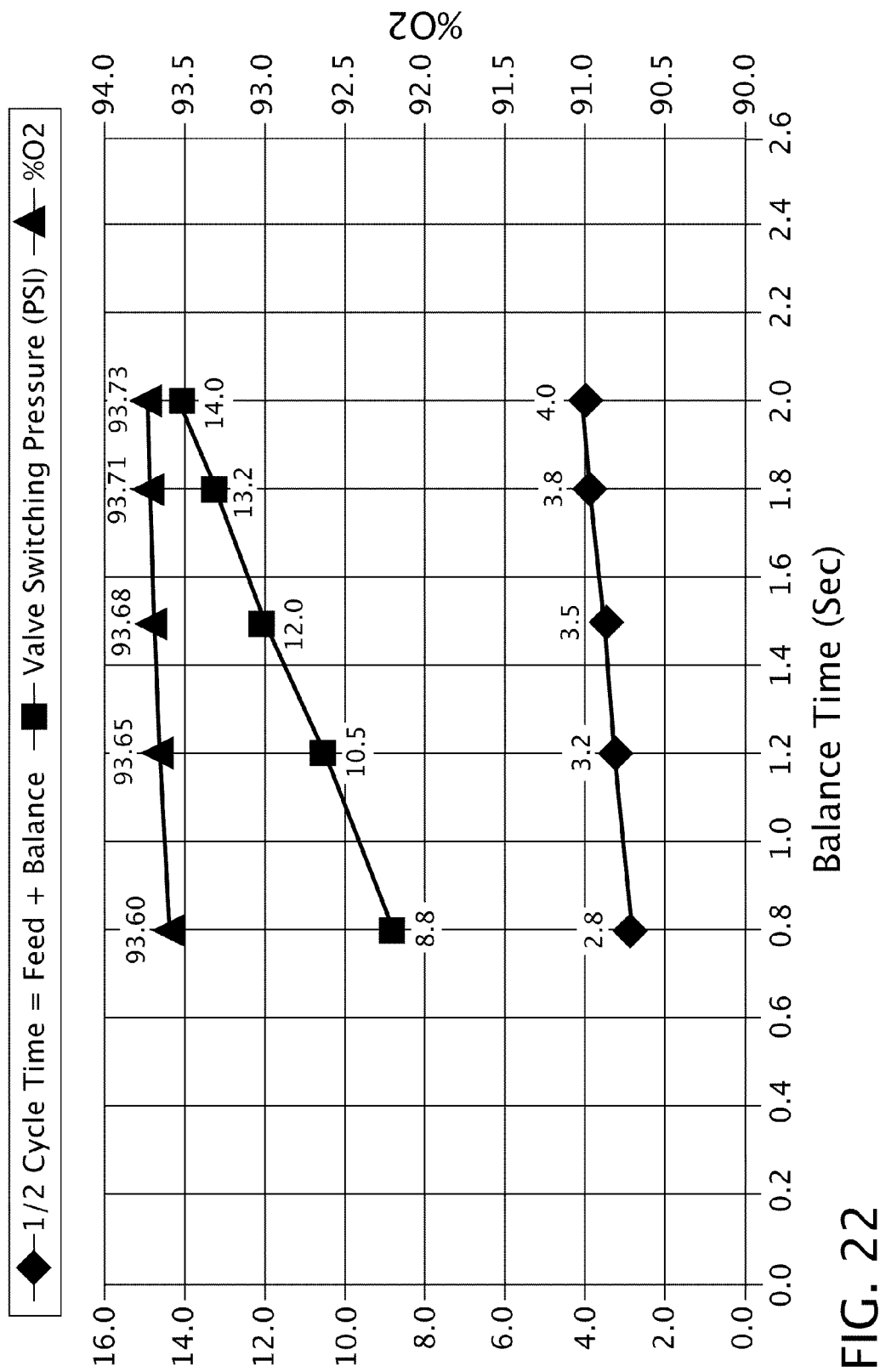
FIG. 22 is a chart of illustrating the relationship between balance time and the switching pressures and oxygen output concentration an embodiment of the pressure swing adsorption system according to the principles of the present invention.

FIG. 22 provides a chart illustrating the relationship between balance time and the switching pressures and oxygen output concentration an embodiment of pressure swing adsorption system 100. As illustrated by the data graphed in FIG. 22, an extension of the balance time increases both the oxygen concentration of the output of an embodiment of the pressure swing adsorption system and the switching pressures of the system. For example, and not limitation, an extended balance time of 2 seconds results in a switching pressure of 14 psi an oxygen concentration of 93.73%. This is an improvement from conventional balance time duration of 0.8 seconds, which results in a switching pressure of 8.8 psi and an oxygen concentration of 93.60%.

The operation of the pressure swing adsorption system is largely superior to that of the conventional systems. The design, architecture, and feature set of the components of the system allow for a lightweight system that operates more efficiently and produces a higher quality output. For example, and not limitation, matching the design of the compressor to the capacity of the sieve chambers allows for a highly optimized paring of two important components of the pressure swing adsorption system. Therefore, the system is enabled to provide superior product gas generation in a lightweight device. Compared to conventional devices, the pressure swing adsorption system of the present invention is quieter and it does not cycle as often. Furthermore the pressure swing adsorption system of the present invention provides more control and flexibility to the user.

In a exemplary embodiment, pressure swing adsorption system 100 can be operated in an increased oxygen mode, which enables the system to generate oxygen at a purity levels beyond any device in the prior art and even beyond what was perceived by those of skill in the art as a practical maximum. Conventional thinking by those of skill in the art followed the approach that the device should concentrate oxygen less efficiently at lower flow rates. An exemplary embodiment of pressure swing adsorption system 100, however, goes against the conventional logic and relies upon a longer cycle and precise control of the purge device to achieve maximum oxygen generation purities at lower flow rates. Furthermore, an exemplary embodiment of pressure swing adsorption system 100 can be operated to consume minimal power. Therefore, the pressure swing adsorption system can be operated at conventional oxygen purity levels and consume significantly less power than the devices of the prior art. In yet another mode, pressure swing adsorption system 100 can be operated in a sound reduction mode to minimize the amount of sound that the system emits to the ambient environment. The user can manually switch between modes via a manually actuated input, or the system can automatically select the mode depending on the operating characteristics of the system.

The present invention contemplates that pressure swing adsorption system 100 can include additional features typically found in oxygen generating and delivery systems. For example, the present invention contemplates providing on oxygen conserving device (OCD) 190 in the gas stream delivered to the user. In the embodiment shown in FIG. 1, OCD 190 is provided upstream of filter 175. Of course, the present invention contemplates providing it at other suitable locations. OCD 190 can be an electronic or a pneumatic oxygen conserver.

The primary advantage of an OCD in an oxygen concentration system, such as system 100, is to extend the effective maximum flow rate beyond the continuous maximum rating. For example, a system whose sieve beds and compressor system are sized for a continuous maximum flow rate of 1 LPM can be classified effectively as a 3 LPM system when coupled with a 3:1 OCD. This is because the OCD controls the flow of oxygen to the patient, delivering a specific volume of oxygen over a specific period of time, during only the inhalation phase of the breathing cycle. The additional weight, cost, and power consumption of the OCD are small compared to the additional weight, cost and power required to make a larger continuous flow system.

The present invention further contemplates that pressure swing adsorption system 100 can used in part of a larger oxygen generating and delivery and/or storage system. For example, the gas flow output by the PSA system can be used as a source of gas for other systems, such as a gas transfill system or a liquefaction system. In a gas transfill system, the gas from the gas source, which is typically at a pressure of 5-40 psi, is provided to a pressure booster or intensifier system. The pressure intensifier system increases the pressure of the gas to 2000-3000 psi. This high pressure gas is provided to a portable container for use by a patient. Examples of gas transfill systems that are suitable for use with PSA system 100 are described in U.S. Pat. Nos. 5,071,453; 5,858,062; 5,988,165; 6,342,090; 6,446,630; 6,889,726 and 6,904,913; the contents of each of which are incorporated herein by reference.

In one embodiment, the oxygen enriched gas produced by a PSA system is provided as a low pressure oxygen enriched gas stream to both a user and to the pressure intensifying system. The user can breathing on the system from the low pressure oxygen enriched gas stream while the system fills the portable container or increases the pressure of this low pressure gas stream. Such a system is disclosed, for example, in U.S. Pat. No. 5,858,062. In another embodiment, all of the gas in the low pressure oxygen enriched gas stream is provided to the pressure intensifying assembly. The user can breath off of the high pressure gas stream via a pressure regulator and an optional oxygen conserver, even while the high pressure gas stream is being provided to a storage vessel. Such a system is disclosed, for example, in U.S. Pat. No. 6,904,913. In a still further embodiment, the low pressure oxygen enriched gas is provided to a switch, so that this gas stream is provided either to a user or the pressure intensifying system. Such a system is disclosed, for example, in U.S. Pat. No. 6,446,630.

In a liquefaction system, the gas from the gas source is provided to a liquefaction system that liquefies the oxygen enriched gas stream into liquid oxygen (LOX). The LOX is stored or provided to a portable container for use by a patient. Examples of liquefaction systems that are suitable for use with PSA system 100 are described in U.S. Pat. Nos. 5,892,275; 5,979,440; 6,212,904; 6,651,653; 6,681,764; and 6,989,423; and in U.S. patent application Ser. Nos. 11/131,071 (publication no. US 2006/0086099) and 11/130,646 (publication no. US 2006/0086102); the contents of each of which are incorporated herein by reference. As with the gas transfill systems, in one embodiment, the liquefaction systems can enable the user to breath off of the low pressure oxygen enriched gas being provided to the liquefier. In another embodiment, the user can breath of the of the liquid oxygen supply, either from a reservoir in the LOX generating system or from a portable container filled by the LOX system.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An adsorption system (100) for separating air into a concentrated gas component, the system comprising:
   a compressor (115) for receiving and compressing air from an air supply, providing a compressed air supply;
   molecular sieve material for separating the compressed air supply into a concentrated gas component; and
   an outlet delivering at least 95.7% pure concentrated gas component from the molecular sieve material, wherein the capacity of the compressor is matched to the capacity of the molecular sieve material.

2. The system of claim 1, wherein the outlet delivers at least 96% pure concentrated gas component from the molecular sieve material.

3. The system of claim 1, wherein the outlet delivers at least 96.4% pure concentrated gas component from the molecular sieve material.

4. The system of claim 1, wherein the concentrated gas component is oxygen.

5. The system of claim 1, wherein the capacity of the compressor being matched to the capacity of the molecular sieve material includes a rate at which the compressor provides the compressed air supply being matched to a rate at which the molecular sieve material processes the compressed air supply while maintaining a predetermined recovery rate of the concentrated gas component.

6. The system of claim 1, wherein the capacity of the compressor and the capacity of the molecular sieve material are described by a volume per unit time at a given pressure.

7. An adsorption system (100) for separating air into a concentrated gas component, the system comprising:
   a compressor (115) for receiving and compressing air from an air supply, providing a compressed air supply;
   molecular sieve material for separating the compressed air supply into a concentrated gas component;
   a first molecular sieve chamber (130) for receiving the molecular sieve material;
   at second molecular sieve chamber (135) for receiving the molecular sieve material;
   a supply chamber for receiving the compressed air supply and for communicating the compressed air supply to the first and the second molecular sieve chambers;
   an outlet delivering a concentrated gas component from the molecular sieve material; and
   a fixed orifice for communicating the concentrated gas component between the first molecular sieve chamber and the second molecular sieve chamber,
   wherein the molecular sieve material has a total molecular sieve material weight, and wherein the total molecular sieve material weight per square inch of the area of the fixed orifice is less than <3,000 lbs/square inch.

8. An adsorption system (100) for separating air into a concentrated gas component, the system comprising:
   a compressor (115) for receiving and compressing air from an air supply, providing a compressed air supply;
   molecular sieve material for separating the compressed air supply into a concentrated gas component;
   a first molecular sieve chamber (130) for receiving the molecular sieve material;
   a second molecular sieve chamber (135) for receiving the molecular sieve material;
   a supply chamber for receiving the compressed air supply and for communicating the compressed air supply to the first and the second molecular sieve chambers; and
   an outlet delivering a concentrated gas component from the molecular sieve material,
   wherein the capacity of the compressor is matched to the capacity of the molecular sieve material.

9. The system of claim 8, wherein the molecular sieve material is capable of processing a first volume of gas at a first pressure in a first time period and the compressor generates a maximum of the first volume of gas at the first pressure in the first time period.

10. The system of claim 8, wherein the capacity of the compressor being matched to the capacity of the molecular sieve material includes a rate at which the compressor provides the compressed air supply being matched to a rate at which the molecular sieve material processes the compressed air supply while maintaining a predetermined recovery rate of the concentrated gas component.

11. The system of claim 8, wherein the capacity of the compressor and the capacity of the molecular sieve material are described by a volume per unit time at a given pressure.

* * * * *